US012692219B2

(12) United States Patent
Zhong et al.

(10) Patent No.: US 12,692,219 B2
(45) Date of Patent: Jul. 28, 2026

(54) NITRO COMPOUND HYDROGENATION REACTION PROCESS AND HYDROGENATION REACTION APPARATUS

(71) Applicants: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

(72) Inventors: Siqing Zhong, Shanghai (CN); Jun Xu, Shanghai (CN); Le Zhao, Shanghai (CN); Lianghua Wu, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, Shanghai (CN)

(*) Notice: Subject to any disclaimer, the term of this patent is extended or adjusted under 35 U.S.C. 154(b) by 901 days.

(21) Appl. No.: 17/286,666

(22) PCT Filed: Oct. 17, 2019

(86) PCT No.: PCT/CN2019/111641

§ 371 (c)(1),
(2) Date: Apr. 19, 2021

(87) PCT Pub. No.: WO2020/078413

PCT Pub. Date: Apr. 23, 2020

(65) Prior Publication Data

US 2021/0371370 A1 Dec. 2, 2021

(30) Foreign Application Priority Data

Oct. 17, 2018 (CN) ........................ 201811207014.5

(51) Int. Cl.

| | |
|---|---|
| ***C07C 209/36*** | (2006.01) |
| ***B01J 8/00*** | (2006.01) |
| ***B01J 8/08*** | (2006.01) |
| ***B01J 8/18*** | (2006.01) |
| ***B01J 8/24*** | (2006.01) |
| ***B01J 21/08*** | (2006.01) |
| ***B01J 23/72*** | (2006.01) |
| ***B01J 23/94*** | (2006.01) |
| ***B01J 35/40*** | (2024.01) |
| ***B01J 38/06*** | (2006.01) |

(52) U.S. Cl.

CPC .......... *C07C 209/36* (2013.01); *B01J 8/0055* (2013.01); *B01J 8/1809* (2013.01); *B01J 8/1827* (2013.01); *B01J 8/24* (2013.01); *B01J 21/08* (2013.01); *B01J 23/72* (2013.01); *B01J 23/94* (2013.01); *B01J 35/40* (2024.01); *B01J 38/06* (2013.01); *B01J 2208/00752* (2013.01)

(58) Field of Classification Search

CPC .... C07C 209/32; C07C 209/36; B01J 8/1827; B01J 23/72; B01J 2208/00752; B01J 8/24; B01J 21/08; Y02P 20/584

See application file for complete search history.

(56) References Cited

U.S. PATENT DOCUMENTS

| | | | | |
|---|---|---|---|---|
| 2,891,094 | A * | 6/1959 | Karkalits, Jr. | B01J 23/72 502/244 |
| 4,714,689 | A | 12/1987 | Stammann et al. | |
| 5,380,426 | A | 1/1995 | Johnson et al. | |
| 6,652,736 | B1 | 11/2003 | Del Pozo et al. | |
| 2004/0031729 | A1 | 2/2004 | Meier et al. | |
| 2010/0280271 | A1 * | 11/2010 | Sommer | C07C 209/36 564/423 |
| 2012/0065431 | A1 | 3/2012 | Königsmann et al. | |
| 2013/0006018 | A1 | 1/2013 | Mitchell et al. | |
| 2021/0387153 | A1 * | 12/2021 | Zhong | B01J 23/94 |

FOREIGN PATENT DOCUMENTS

| | | | |
|---|---|---|---|
| CN | 1206707 | A | 2/1999 |
| CN | 1270853 | A | 10/2000 |
| CN | 1528737 | A | 9/2004 |
| CN | 1634860 | A | 7/2005 |
| CN | 2757912 | | 2/2006 |

(Continued)

OTHER PUBLICATIONS

CN106732822A—English translation (Year: 2017).*
X.L. Jiang 45 Chlor-Alkali Industry 30-34 (2009) (Year: 2009).*
T. Chandra, et al., 23, Journal of Chemical Health & Safety 16-25 (2016) (Year: 2016).*
M. Orlandi, et al., 22 Organic Process Research & Development 430-445 (2018) (Year: 2018).*
J. Werther, Ullmann's encyclopedia of industrial chemistry, (2000) (Year: 2000).*
S. Diao, et al. 286 Applied Catalysis A: General 30-35 (2005)("Diao") (Year: 2005).*
Le Huy Anh; "Vietnam Office Action for Applicaiton No. 1-2021-02594"; Ministry of Science and Technology, The National Office of Intellectual Property, the Socialist Republic of Vietnam; hanoi, Aug. 29, 2023; pp. 1-2.
Jiang, Xinliang; "Application of Cu—SiO2 catalyst in aminobenzene production"; Chlor-Alkali Industry; vol. 45, No. 9; Sep. 15, 2009; pp. 30-34.

(Continued)

*Primary Examiner* — Alexander R Pagano
*Assistant Examiner* — Frank S. Hou
(74) *Attorney, Agent, or Firm* — NKL Law; Allen Xue

(57) ABSTRACT

The present invention relates to a nitro compound hydrogenation reaction process and hydrogenation reaction apparatus, which can achieve the objects of the continuous reaction of the nitro compound and the long-period run of regeneration and activation. The nitro compound hydrogenation reaction process comprises a hydrogenation step, a regeneration step, an optional activation step and a recycling step. There exists at least one step of degassing the spent catalyst between the hydrogenation step and the regeneration step. According to circumstances, there exists at least one step of degassing the regenerated catalyst between the regeneration step and the activation step.

11 Claims, 1 Drawing Sheet

(56) References Cited

FOREIGN PATENT DOCUMENTS

| | | | | |
|---|---|---|---|---|
| CN | 1754625 | A | | 4/2006 |
| CN | 1762567 | A | | 4/2006 |
| CN | 101016247 | A | | 8/2007 |
| CN | 101474582 | | | 7/2009 |
| CN | 106732822 | A | * | 5/2017 |
| CN | 106866429 | A | | 6/2017 |
| JP | S6253745 | | | 3/1987 |
| JP | 2010260858 | | | 11/2010 |
| JP | 2013537480 | | | 10/2013 |
| JP | 2022505350 | | | 1/2022 |
| RU | 2484895 | C2 | | 6/2013 |
| SU | 1109190 | A1 | | 8/1984 |
| WO | 2012013677 | A1 | | 2/2012 |

* cited by examiner

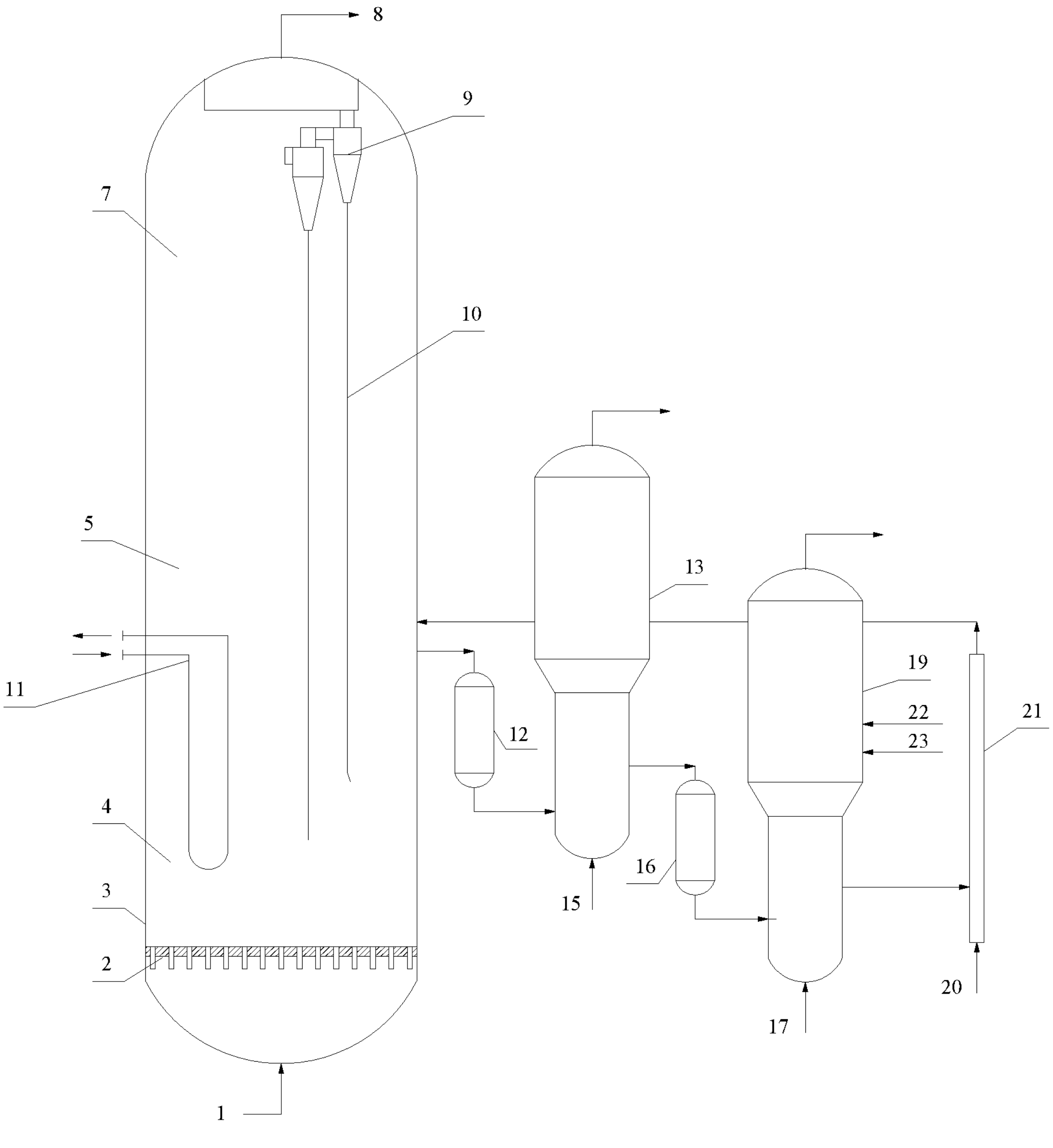
8
9
7
10
5
13
19
11
12
22
23
21
4
16
3
15
2
20
17
1

NITRO COMPOUND HYDROGENATION REACTION PROCESS AND HYDROGENATION REACTION APPARATUS

TECHNICAL FIELD

The present invention relates to a nitro compound hydrogenation reaction process, especially a process for producing aniline by the nitrobenzene hydrogenation. The present invention also relates to a nitro compound hydrogenation reaction apparatus.

BACKGROUND TECHNOLOGY

Aniline is an important basic organic chemical raw material and a fine chemical intermediate, can be used in producing more than 300 downstream products, and is widely used in the industries of dyes, medicines, pesticides, explosives, spices, rubbers, synthetic materials and the like. In recent years, with the rapid rise of polyurethane industry in China and worldwide, aniline, which is one of the nonreplaceable basic raw material for its main raw material MDI (4,4-diphenylmethane diisocyanate), has been developed remarkably and rapidly.

There are three commercial processes for producing aniline: nitrobenzene catalytic hydrogenation process, phenol ammoniation process and iron powder reduction process. Among others, the iron powder reduction process is gradually eliminated due to poor quality of the formed aniline. The phenol ammoniation process is strongly dependent on the source of the phenol. The current nitrobenzene catalytic hydrogenation process is adopted by most of manufacturers. The nitrobenzene catalytic hydrogenation process is also divided into a gas phase catalytic hydrogenation process and a liquid phase catalytic hydrogenation process. The nitrobenzene liquid phase catalytic hydrogenation process is mainly performed by adopting a noble metal catalyst under an anhydrous condition, and has the advantages of low reaction temperature, high catalyst load, long service life and large plant production capacity, and has the disadvantages of high required pressure, necessary separation of reactants from the catalyst and the solvent, high plant operation cost, high catalyst price, and relatively many byproducts caused by too high catalyst activity. The fluidized bed gas phase catalytic hydrogenation process is characterized by that the nitrobenzene as raw material is heated and vaporized, and mixed with hydrogen gas, then fed into the fluidized bed reactor in which the copper-silica gel catalyst is contained to perform the hydrogenation and reduction reaction. This process has the advantages of better improving the heat transfer condition, controlling the reaction temperature, avoiding the local overheating, reducing the formation of the side reaction, and prolonging the service life of the catalyst, and has the disadvantages of the relatively complicated operation, the heavily worn-out catalyst, and the relatively high operation and maintenance costs.

The gas phase hydrogenation process to prepare aniline from nitrobenzene has been used in China for decades, and the fluidized bed gas phase catalytic hydrogenation process is adopted by many aniline manufacturers in China.

Chinese patent application CN1528737A discloses an apparatus, mainly comprising a fluidized bed reactor, a reaction raw material gas inlet arranged at the bottom of the reactor, a first gas distributor arranged at the upper part of the inlet, a second gas distributor arranged at the middle part of the axial-direction height of the reactor and dividing the reactor into two catalyst dense-phase zones, a heat exchanger arranged in two catalyst dense-phase zones inside the reactor; a catalyst overflow device arranged outside or inside the reactor and connecting to the upper and lower two catalyst dense-phase zones respectively, and a gas-solid separation device. Chinese patent application CN1634860A discloses a gas distributor in a fluidized bed for aniline synthesis and a process for synthesizing aniline, wherein the gas distributor is composed of a main pipe for conveying a gas, branch pipes and an annular pipe connected thereto for distributing the gas, and nozzles for injecting the gas downwards and nozzles for injecting the gas upwards both arranged on the annular pipe.

SUMMARY OF THE INVENTION

The inventors of the present invention have found that in the fluidized bed reactor for preparing aniline in the prior art, reaction gas raw materials enter the fluidized bed from a distributor at the bottom and contact with the catalyst to react and to generate aniline as a product gas, and the catalyst is easy to deposit carbon and deactivate, so that the fluidized bed reactor needs to be stopped for regeneration and activation at intervals and is difficult to operate for a long period. Therefore, the key to solve the problem of long-period operation of the aniline reactor is the capability of completing the regeneration and activation of the aniline catalyst in time and on line.

The inventors of the present invention have also found that, in the reaction, regeneration and activation processes, three different components, namely nitrobenzene and hydrogen, oxygen and hydrogen, need to be introduced respectively, wherein when oxygen is in contact with flammable and explosive gases, explosion risks easily occur, therefore after these three stages are finished, each previous stage needs to be efficiently degassed, so that the raw material gas and the product gas entrained in catalyst particles coming from the reactor are effectively removed, the catalyst particles enter the regeneration unit and are regenerated, the air (oxygen) entrained in catalyst particles flowing out of the regeneration reactor is removed, and then the catalyst particles enter the activation unit.

The inventors of the present invention have also found that internal components are generally arranged in the existing aniline fluidized bed reactor and used for adjusting the interior gas-solid flow, but since the aniline catalyst is low in strength and very easy to break, the particle size is gradually reduced along with the operation time, and fine powder is easily immersed into a dilute phase zone and then the load of a cyclone separator is increased, so that the catalyst loss becomes relatively serious, and the subsequent influence is that the reaction cannot be operated for a long period, and the various problems such as the necessity of shutting down and supplementing the catalyst are caused.

The inventors of the present invention believe that the presence of fine powder in the aniline fluidized bed reactor is inevitable. On one hand, it is based on the loss amount to timely supplement the fresh catalyst to maintain the demand for the reaction. On the other hand, since the loss of the fine powder has a greater impact on the fluidization quality of the bed, at the same time, it is necessary to supplement the fine powder catalyst at the appropriate time to maintain the high-efficiency fluidization quality in the reaction zone and to maintain the inherent transmission efficiency. In addition, partial deactivation of the catalyst in the aniline fluidized bed reactor is inevitable. Therefore, the key to solve the problem of long-period operation of the aniline reactor is the capability of completing the regeneration and activation of the aniline catalyst in time and on line.

The present invention has been completed based on these findings.

Specifically, the present invention relates to the following aspects:

1. A nitro compound hydrogenation reaction process, comprising a hydrogenation step, a regeneration step, an optional activation step and a recycling step, which is characterized in that in the hydrogenation step, a nitro compound (especially nitrobenzene) as the reaction raw material is contacted with hydrogen gas and a hydrogenation catalyst in a reactor (referred to as hydrogenation reactor, preferably a fluidized bed reactor) to obtain a reaction product (for example an amino compound, especially aniline) and a spent catalyst, in the regeneration step, the spent catalyst is regenerated in a reactor (referred to as regeneration reactor, preferably a fluidized bed reactor) to obtain a regenerated catalyst, in the optional activation step, the regenerated catalyst is activated in a reactor (referred to as activation reactor, preferably a fluidized bed reactor) to obtain an activated catalyst, in the recycling step, the regenerated catalyst and/or the activated catalyst are recycled (preferably recycled with a lifting pipe) to the hydrogenation step, wherein there exists at least one step of degassing the spent catalyst (referred to as hydrogenation degassing step) between the hydrogenation step and the regeneration step, and (1) in the case that the activation step exists, there exists at least one step of degassing the regenerated catalyst (referred to as first regeneration degassing step) between the regeneration step and the activation step, optionally there exists at least one step of degassing the activated catalyst (referred to as activation degassing step) between the activation step and the recycling step, and optionally there exists at least one step of degassing the regenerated catalyst (referred to as second regeneration degassing step) between the regeneration step and the recycling step, or (2) in the case that the activation step is absent, there exists at least one step of degassing the regenerated catalyst (referred to as third regeneration degassing step) between the regeneration step and the recycling step.
2. The hydrogenation reaction process according to any of the above-mentioned or the afterward-mentioned aspects, wherein assuming that the average mass flowrate (the unit is kg/h) of the spent catalyst being transported from the hydrogenation step to the hydrogenation degassing step is A1, the average mass flowrate (the unit is kg/h) of the spent catalyst being transported from the hydrogenation degassing step to the regeneration step is B1, the average mass flowrate (the unit is kg/h) of the regenerated catalyst being transported from the regeneration step to the first regeneration degassing step is A2, the average mass flowrate (the unit is kg/h) of the regenerated catalyst being transported from the first regeneration degassing step to the activation step is B2, the average mass flowrate (the unit is kg/h) of the activated catalyst being transported from the activation step to the activation degassing step is A3, the average mass flowrate (the unit is kg/h) of the activated catalyst being transported from the activation degassing step to the recycling step is B3, the average mass flowrate (the unit is kg/h) of the regenerated catalyst being transported from the regeneration step to the second regeneration degassing step is A4, the average mass flowrate (the unit is kg/h) of the regenerated catalyst being transported from the second regeneration degassing step to the recycling step is B4, the average mass flowrate (the unit is kg/h) of the regenerated catalyst being transported from the regeneration step to the third regeneration degassing step is A5, the average mass flowrate (the unit is kg/h) of the regenerated catalyst being transported from the third regeneration degassing step to the recycling step is B5, the average mass flowrate (the unit is kg/h) of the regenerated catalyst or the activated catalyst being transported from the recycling step to the hydrogenation step is A6, then at least one (preferably all) of A1 to A6 and B1 to B5 are 5-100 kg/h (preferably 10-30 kg/h).
3. The hydrogenation reaction process according to any of the above-mentioned or the afterward-mentioned aspects, wherein assuming the particle volume fraction (the unit is %) in the transportation pipeline of the spent catalyst being transported from the hydrogenation step to the hydrogenation degassing step is C1, the particle volume fraction (the unit is %) in the transportation pipeline of the spent catalyst being transported from the hydrogenation degassing step to the regeneration step is D1, the particle volume fraction (the unit is %) in the transportation pipeline of the regenerated catalyst being transported from the regeneration step to the first regeneration degassing step is c2, the particle volume fraction (the unit is %) in the transportation pipeline of the regenerated catalyst being transported from the first regeneration degassing step to the activation step is D2, the particle volume fraction (the unit is %) in the transportation pipeline of the activated catalyst being transported from the activation step to the activation degassing step is C3, the particle volume fraction (the unit is %) in the transportation pipeline of the activated catalyst being transported from the activation degassing step to the recycling step is D3, the particle volume fraction (the unit is %) in the transportation pipeline of the regenerated catalyst being transported from the regeneration step to the second regeneration degassing step is C4, the particle volume fraction (the unit is %) in the transportation pipeline of the regenerated catalyst being transported from the second regeneration degassing step to the recycling step is D4, the particle volume fraction (the unit is %) in the transportation pipeline of the regenerated catalyst being transported from the regeneration step to the third regeneration degassing step is C5, the particle volume fraction (the unit is %) in the transportation pipeline of the regenerated catalyst being transported from the third regeneration degassing step to the recycling step is D5, the particle volume fraction (the unit is %) in the transportation pipeline of the regenerated catalyst or the activated catalyst being transported from the recycling step to the hydrogenation step is C6, then at least one (preferably all) of C1 to C6 and D1 to D5 are 0.1-15% (preferably 0.5-5%).
4. The hydrogenation reaction process according to any of the above-mentioned or the afterward-mentioned aspects, wherein the reaction conditions of the hydrogenation step comprise: the superficial gas velocity is 0.2-0.8 m/s (preferably 0.3-0.6 m/s), the molar ratio of hydrogen gas to the reaction raw material (for example nitrobenzene) is 6-21, the reaction temperature is 220-280° C., the reaction pressure is 0.05-1 MPa (gauge pressure), and/or, the reaction conditions of the regeneration step comprise: in the presence of oxygen-containing gas (for example air or oxygen gas), the superficial gas velocity is 0.1-0.6 m/s (preferably 0.2-0.4 m/s), the reaction temperature is 350-450° C., the reaction pressure is 0.05-1 MPa (gauge pressure), and/or, the reaction conditions of the activation step comprise: in the presence of hydrogen gas, the superficial gas velocity is 0.1-0.6 m/s, the reaction temperature is 200-250° C., the reaction pressure is 0.05-1 MPa (gauge pressure).

5. The hydrogenation reaction process according to any of the above-mentioned or the afterward-mentioned aspects, wherein the dimensionless particle diameter of the hydrogenation reactor is in the range of 1-60, and/or, the dimensionless particle diameter of the regeneration reactor is in the range of 1-40, and/or, the dimensionless particle diameter of the activation reactor is in the range of 1-30, wherein the dimensionless particle diameter is determined by the following equation:

$$\text{Dimensionless particle diameter} = \text{Average particle diameter} \times \sqrt[3]{\frac{\text{Gas density} \times \text{Gas} - \text{solid density difference} \times g}{\text{Gas kinetic viscosity}^2}},$$

Wherein, the average particle diameter is the volume average particle diameter (the unit is m) of solid particles in the reactor, the gas density is the density (the unit is $kg/m^3$) of the gas in the reactor, the gas-solid density difference is the difference of the density (the unit is $kg/m^3$) of solid particles minus the density (the unit is $kg/m^3$) of the gas in the reactor, the gas kinetic viscosity is the kinetic viscosity (the unit is Pa·s) of the gas in the reactor, and g is the absolute value of the gravity acceleration (9.8 $m/s^2$).

6. The hydrogenation reaction process according to any of the above-mentioned or the afterward-mentioned aspects, which further comprises a step of transporting a supplement hydrogenation catalyst to at least one of the hydrogenation step, the regeneration step, the optional activation step and the recycling step, and preferably comprises a step of transporting a supplement hydrogenation catalyst to the activation step (referred to as catalyst supplement step).

7. The hydrogenation reaction process according to any of the above-mentioned or the afterward-mentioned aspects, wherein in the catalyst supplement step, the ratio of the average mass flowrate of the supplement hydrogenation catalyst being transported to the hydrogenation catalyst inventory in the hydrogenation reactor (the unit is kg) is 0-10 $h^{-1}$ (preferably 0.00002-0.001 $h^{-1}$).

8. The hydrogenation reaction process according to any of the above-mentioned or the afterward-mentioned aspects, wherein the hydrogenation reactor is a fluidized bed reactor, the fluidized bed reactor comprise a dense phase reaction zone (4), at least one dynamic pressure measuring point (preferably the response frequency is not less than 100 Hz) is mounted on the side wall of the dense phase reaction zone (4) to measure the instantaneous pressure fluctuation in the dense phase reaction zone (4), when the standard deviation of the instantaneous pressure fluctuation is greater than 600 Pa (preferably greater than 1500 Pa), the catalyst supplement step is initiated, and/or, the hydrogenation reactor is a fluidized bed reactor, the fluidized bed reactor comprises a dense phase reaction zone (4), when the catalyst particles having a particle diameter of less than 100 μm comprise greater than 3 wt % (preferably greater than 5 wt %) by mass percent of all catalyst particles in the dense phase reaction zone (4), the catalyst supplement step is initiated.

9. The hydrogenation reaction process according to any of the above-mentioned or the afterward-mentioned aspects, wherein the supplement hydrogenation catalyst is selected from at least one of a copper-based loaded catalyst, a nickel-based loaded catalyst and a noble metal-based loaded catalyst, having an average particle diameter of 5-150 μm (preferably 20-70 μm).

10. The hydrogenation reaction process according to any of the above-mentioned or the afterward-mentioned aspects, wherein the hydrogenation catalyst is selected from at least one of a copper-based loaded catalyst, a nickel-based loaded catalyst and a noble metal-based loaded catalyst, and/or, the hydrogenation catalyst has a bulk density of 300-1200 $kg/m^3$, and/or, the hydrogenation catalyst has an average particle diameter of 30-800 μm (preferably 40-500 μm or 50-600 μm), and the catalyst particles having a particle diameter of less than 80 μm comprise not less than 2 wt % (preferably 5-15 wt %) by mass percent of all catalyst particles, and/or, the nitro compound is selected from at least one of the compounds represented by the following formula (1), $$R—NO_2 \quad (1)$$

In the structural formula (1), R is an optionally substituted $C_{2-20}$ straight, branched or cyclic hydrocarbyl (preferably an optionally substituted $C_{4-20}$ cyclic hydrocarbyl, especially an optionally substituted $C_{6-20}$ aryl, more especially an optionally substituted phenyl).

11. A hydrogenation reaction apparatus of the nitro compound, comprising a hydrogenation reactor (preferably a fluidized bed reactor), a regeneration reactor (preferably a fluidized bed reactor), an activation reactor (preferably a fluidized bed reactor) and a recycling unit (for example a lifting pipe), the hydrogenation reactor is communicated with the regeneration reactor via at least one spent catalyst degasser through transportation pipelines, the regeneration reactor is communicated with the activation reactor via at least one regenerated catalyst degasser through transportation pipelines, the activation reactor is communicated with the recycling unit through transportation pipelines or communicated with the recycling unit via at least one activated catalyst degasser through transportation pipelines, the recycling unit is communicated with the hydrogenation reactor through transportation pipelines, wherein the solid particle inventory (the unit is kg) of the hydrogenation reactor: the solid particle inventory (the unit is kg) of the regeneration reactor:solid particle inventory (the unit is kg) of the activation reactor=(10-200):(0.1-20):(0.1-20) (preferably (20-100):(0.5-8):(0.5-8)).

12. The hydrogenation reaction apparatus according to any of the above-mentioned or the afterward-mentioned aspects, wherein the hydrogenation reactor has a height of 5-60 m (preferably 10-30 m), and a diameter of 0.5-12 m (preferably 1-8 m), and/or, the regeneration reactor has a height of 1-15 m (preferably 3-6 m), and a diameter of 0.1-3 m (preferably 0.3-1 m), and/or, the activation reactor has a height of 1-15 m (preferably 3-6 m), and a diameter of 0.1-3 m (preferably 0.3-1 m), and/or, the inner diameters of the transportation pipelines are, identical to or different from each other, each independently 30-400 mm (preferably 50-300 mm).

On the other hand, the present invention relates to the following aspects:

1. A reaction apparatus for producing aniline by the nitrobenzene hydrogenation, comprising: a fluidized bed reactor (3), a degassing tank for the spent catalyst (12), a regenerator (13), a degassing tank for the catalyst to be activated (16), an activator (19) and a lifting pipe (21), wherein a dense phase reaction zone (4) located in the lower section, a particle sputtering transition zone (5) located in the middle section and a dilute-phase zone (7) located in the upper section are included in the fluidized bed reactor (3), the degassing tank for the spent catalyst (12) is communicated with the fluidized bed reactor (3) and the regenerator (13) respectively, the degassing tank for the catalyst to be activated (16) is communicated with the regenerator (13) and the activator (19) respectively, a lifting pipe (21) is communicated with the activator (19) and the fluidized bed reactor (3) respectively.
2. The reaction apparatus for producing aniline by the nitrobenzene hydrogenation according to any of the above-mentioned or the afterward-mentioned aspects, which is characterized in that in the fluidized bed reactor (3) are provided a gas distributor (2), a heat-exchanging pipe (11), a sputtering separation member (6) and a cyclone separator (9).
3. The reaction apparatus for producing aniline by the nitrobenzene hydrogenation according to any of the above-mentioned or the afterward-mentioned aspects, which is characterized in that in the degassing tank for the spent catalyst (12) are included a degassing descending countercurrent zone (31) and a degassing ascending co-current zone (32), and in the degassing descending countercurrent zone (31) and the degassing ascending co-current zone (32) are respectively provided degassing baffle members (33); in the degassing tank for the catalyst to be activated (16) are included a regeneration degassing descending countercurrent zone (51) and a regeneration degassing ascending co-current zone (52), and in the regeneration degassing descending countercurrent zone (51) and the regeneration degassing ascending co-current zone (52) are respectively provided degassing baffle members (33).
4. The reaction apparatus for producing aniline by the nitrobenzene hydrogenation according to any of the above-mentioned or the afterward-mentioned aspects, which is characterized in that the degassing baffle member (33) is made by connecting multiple sets of flow rectifiers through connecting pieces, the flow rectifier is one or more of a streamline flow rectifier (41), a diamond-shaped flow rectifier (42), and an inclined baffle cross-flow type flow rectifier (43).
5. A reaction process for producing aniline by the nitrobenzene hydrogenation with the apparatus according to any of the above-mentioned or the afterward-mentioned aspects, comprising the following steps:

(a). vaporized nitrobenzene and hydrogen gas as raw material are introduced into a gas chamber, then into the fluidized bed reactor (3) through the gas distributor (2) to push the catalyst in the reactor to be fluidized, then react in the dense phase reaction zone (4) to produce an aniline product, the particle sputtering occurs at the top of the dense phase reaction zone (4) to form a particle sputtering transition zone (5), the sputtered particles are efficiently intercepted by the sputtering separation member (6) and return to the dense phase reaction zone (4) to proceed with the catalysis, a small part of the non-intercepted particles pass through the passage of the sputtering separation member and enter the dilute-phase zone (7) to be separated with a cyclone separator (9), the particles return to the dense phase reaction zone (4), the crude product gas (8) flows out of the fluidized bed reactor (3) and is sent into the subsequent separation section;

(b). After the catalyst is partly coked in the reaction, the coked catalyst is degassed in the degassing tank for the spent catalyst (12), and introduced into the regenerator (13), to which the oxygen is introduced, the catalyst is regenerated by carbon burning;

(c). The regenerated catalyst is then introduced into the degassing tank for the catalyst to be activated (16) and degassed, and then introduced into the activator (19), to which hydrogen gas is introduced, the catalyst is activated, and the activated catalyst is introduced into the lifting pipe (21), and lifted up to return to the fluidized bed reactor (3) to proceed with the catalysis.

6. The reaction process for producing aniline by the nitrobenzene hydrogenation according to any of the above-mentioned or the afterward-mentioned aspects, which is characterized in that the catalyst was a metal loaded catalyst with copper as the main active component, the support is alumina or silica, the catalyst has an average particle diameter of 50-600 μm, and the content of particles lower than 80 μm is not less than 2%.
7. The reaction process for producing aniline by the nitrobenzene hydrogenation according to any of the above-mentioned or the afterward-mentioned aspects, which is characterized in that the reaction conditions in the fluidized bed reactor (3) comprise: the superficial gas velocity is 0.2-0.8 m/s, the molar ratio of hydrogen gas to nitrobenzene is 6-21, the average reaction temperature in the dense phase reaction zone (4) is controlled at 220-280° C., the temperature in the vicinity of the gas distributor (2) is controlled at 320° C. or less, the reaction pressure in the dense phase reaction zone (4) is 0.05-1 MPa.
8. The reaction process for producing aniline by the nitrobenzene hydrogenation according to any of the above-mentioned or the afterward-mentioned aspects, which is characterized in that the reaction conditions in the regenerator (13) comprise: the superficial gas velocity is 0.1-0.6 m/s, and the average regeneration temperature is 350-450° C.; the reaction conditions in the activator (19) comprise: the superficial gas velocity is 0.1-0.6 m/s, the average activation temperature is 200-250° C.
9. The reaction process for producing aniline by the nitrobenzene hydrogenation according to any of the above-mentioned or the afterward-mentioned aspects, which is characterized in that the ratio of the superficial gas velocity of the degassing descending countercurrent zone (31) to the superficial gas velocity of the degassing ascending co-current zone (32) in the degassing tank for the spent catalyst (12) is 1/15-1, the degassing agent is one or more (as mixture) of nitrogen gas, water vapor, carbon dioxide, methane, and argon gas, the gas component carried over from the fluidized bed reactor (3) is replaced out.

10. The reaction process for producing aniline by the nitrobenzene hydrogenation according to any of the above-mentioned or the afterward-mentioned aspects, which is characterized in that the ratio of the superficial gas velocity of the regeneration degassing descending countercurrent zone (51) to the superficial gas velocity of the regeneration degassing ascending co-current zone (52) in the degassing tank for the catalyst to be activated (16) is 1/15-1, the degassing agent is one or more (as mixture) of nitrogen gas, water vapor, carbon dioxide, oxygen gas, and argon gas, the oxygen-containing gas component carried over from the regenerator (13) is replaced out.

Technical Effect

According to the hydrogenation reaction process and the hydrogenation reaction apparatus of the present invention, the object of the long-period run of the continuous reaction, regeneration and activation is achieved by the continuous regeneration and activation of the coked catalyst.

According to the hydrogenation reaction process and the hydrogenation reaction apparatus of the present invention, the steady run of the production is realized by supplementing the catalyst in a targeted manner.

BRIEF DESCRIPTION OF THE DRAWINGS

FIG. 1 is a schematic flow diagram of the nitro compound hydrogenation reaction process and hydrogenation reaction apparatus of the present invention, in which a process and apparatus for producing aniline by the nitrobenzene hydrogenation is taken as an example.

In FIG. 1, 1: raw material of vaporized nitrobenzene and hydrogen gas; 2: gas distributor; 3: fluidized bed reactor; 4: dense-phase reaction zone; 7: dilute-phase zone; 8: crude product gas; 9: cyclone separator; 10: dipleg; 11: heat-exchanging pipe; 12: degassing tank for the spent catalyst; 13: regeneration reactor; 15: fluidization gas for regeneration; 16: degassing tank for the catalyst to be activated; 17: fluidization gas for activation; 19: activation reactor; 20: lifting gas; 21: lifting pipe; 22: supplement fine particle feed inlet; 23: supplement fresh catalyst feed inlet.

DETAILED DESCRIPTION

Reference will now be made in detail to the present embodiments of the present invention, but it should be understood that the scope of the invention is not limited by the embodiments, but is defined by the appended claims.

All publications, patent applications, patents, and other references mentioned in this specification are herein incorporated by reference in their entirety. Unless defined otherwise, all technical and scientific terms used herein have the same meanings as commonly understood by those skilled in the art to which this invention belongs. In case of conflict, the present specification, including definitions, will control.

When the specification derives a material, a substance, a process, a step, a device, an element and the like with the expression such as "known to those skilled in the art", "prior art", or the analogous term, it is intended that the subject matter so derived encompasses those having been conventionally used in the art at the time of filing this application, but also includes those which may not be so commonly used at the present time, but will become known in the art as being suitable for a similar purpose.

In the context of the present specification, the term "substantially" means the allowance of the presence of a deviation acceptable to those skilled in the art or considered reasonable by those skilled in the art, for example, a deviation within ±10%, within ±5%, within ±1%, within ±0.5% or within ±0.10%.

In the context of the present specification, the expression "optionally substituted" refers to optionally substituted by one or more (for example 1-5, 1-4, 1-3, 1-2 or 1) substituent groups selected from halogen, hydroxy, mercapto, amino, aminocarbonyl, nitro, oxo, thio, cyano, $C_{1-6}$ linear or branched (halo) alkane (oxy, thio, amino, carbonyl) group, $C_{2-6}$ linear or branched (halo) alkene (oxy, thio, amino, carbonyl) group, $C_{2-6}$ linear or branched (halo) alkyne (oxy, thio, amino, carbonyl) group, $C_{3-20}$ cycloalkyl, $C_{3-20}$ cycloalkane (oxy, thio, amino) group, $C_{3-20}$ cycloalkyl $C_{1-6}$ linear or branched (halo) alkane (oxy, thio, amino, carbonyl) group, $C_{3-20}$ cycloalkyl $C_{2-6}$ linear or branched (halo) alkene (oxy, thio, amino, carbonyl) group, $C_{3-20}$ cycloalkyl $C_{2-6}$ linear or branched (halo) alkyne (oxy, thio, amino, carbonyl) group, $C_{3-20}$ cycloalkenyl, $C_{3-20}$ cycloalkene (oxy, thio, amino) group, $C_{3-20}$ cycloalkenyl $C_{1-6}$ linear or branched (halo) alkane (oxy, thio, amino, carbonyl) group, $C_{3-20}$ cycloalkenyl $C_{2-6}$ linear or branched (halo) alkene (oxy, thio, amino, carbonyl) group, $C_{3-20}$ cycloalkenyl $C_{2-6}$ linear or branched (halo) alkyne (oxy, thio, amino, carbonyl) group, $C_{6-20}$ aryl, $C_{6-20}$ arene (oxy, thio, amino) group, $C_{6-20}$ aryl $C_{1-6}$ linear or branched (halo) alkane (oxy, thio, amino, carbonyl) group, $C_{6-20}$ aryl $C_{2-6}$ linear or branched (halo) alkene (oxy, thio, amino, carbonyl) group, $C_{6-20}$ aryl $C_{2-6}$ linear or branched (halo) alkyne (oxy, thio, amino, carbonyl) group, $C_{4-20}$ heteroaryl, $C_{4-20}$ heteroarene (oxy, thio, amino) group, $C_{4-20}$ heteroaryl $C_{1-6}$ linear or branched (halo) alkane (oxy, thio, amino, carbonyl) group, $C_{4-20}$ heteroaryl $C_{2-6}$ linear or branched (halo) alkene (oxy, thio, amino, carbonyl) group, $C_{4-20}$ heteroaryl $C_{2-6}$ linear or branched (halo) alkyne (oxy, thio, amino, carbonyl) group, $C_{2-20}$ heterocyclyl, $C_{2-20}$ heterocycle (oxy, thio, amino) group, $C_{2-20}$ heterocyclyl $C_{1-6}$ linear or branched (halo) alkane (oxy, thio, amino, carbonyl) group, $C_{2-20}$ heterocyclyl $C_{2-6}$ linear or branched (halo) alkene (oxy, thio, amino, carbonyl) group and $C_{2-20}$ heterocyclyl $C_{2-6}$ linear or branched (halo) alkyne (oxy, thio, amino, carbonyl) group. When a plurality of these substituent groups are present, two adjacent substituent groups (for example the molecular chain ends of two substituent groups) can be bonded to each other to form a divalent substituent group structure. For example, two adjacent $C_{1-6}$ linear or branched alkyl groups can be bonded to each other to form a corresponding alkylene structure. Or, two adjacent $C_{1-6}$ linear or branched alkyloxy groups for example can form a corresponding alkylenedioxy group structure, two adjacent $C_{1-6}$ linear or branched alkylamino groups for example can form a corresponding alkylenediamino structure, two adjacent $C_{1-5}$ linear or branched alkylthio groups for example can form a corresponding alkylenedithio structure, and so forth. As the preferred substituent group, for example, halogen, hydroxy, mercapto, amino, thio, oxo or $C_{1-6}$ linear or branched (halo) alkane (oxy, thio, amino, carbonyl) group and others can be enumerated. Herein, the expression "(halo) alkane (oxy, thio, amino, carbonyl) group" means: alkyl, haloalkyl, alkyloxy, alkylthio, alkylamino, alkylcarbonyl, haloalkyloxy, haloalkylthio, haloalkylamino or haloalkylcarbonyl, the expression "(halo) alkene (oxy, thio, amino, carbonyl) group" means: alkenyl, haloalkenyl, alkenyloxy, alkenylthio, alkenylamino, alkenylcarbonyl, haloalkenyloxy, haloalkenylthio, haloalkenylamino or haloalkenylcarbonyl, the expression "(halo) alkyne (oxy, thio, amino, carbonyl) group" means: alkynyl, haloalkynyl, alkynyloxy, alkynylthio, alkynylamino, alkynylcarbonyl, haloalkynyloxy, haloalkynylthio, haloalkynylamino or haloalkynylcarbonyl, the expression "(oxy, thio, amino) group" means oxy, thio or amino. Here, the expression "halo" includes monohalo, dihalo, trihalo, or perhalo, and the like.

All percentages, parts, ratios, and the like referred to within this specification are by weight and pressures are gauge pressures unless explicitly indicated.

In the context of this specification, any two or more embodiments of the present invention may be combined in any combination, and the resulting technical solution is part of the original disclosure of this specification, and is within the scope of the present invention.

One embodiment according to the present invention relates to a nitro compound hydrogenation reaction process. The hydrogenation reaction process comprises a hydrogenation step, a regeneration step, an activation step and a recycling step. Herein, the activation step is an optional step.

According to one embodiment of the present invention, in the hydrogenation step, a nitro compound and hydrogen gas as the reaction raw material are contacted with a hydrogenation catalyst in the reactor to obtain a reaction product and a spent catalyst. Herein, as the reactor, a fluidized bed reactor is preferable, especially a reactor having a fluidized bed of catalyst particles.

According to one embodiment of the present invention, in the regeneration step, the spent catalyst is regenerated in a reactor (referred to as regeneration reactor) to obtain a regenerated catalyst. Herein, as the reactor, a fluidized bed reactor is preferable.

According to one embodiment of the present invention, in the activation step, the regenerated catalyst is activated in a reactor (referred to as activation reactor) to obtain an activated catalyst.

Herein, as the reactor, a fluidized bed reactor is preferable.

According to one embodiment of the present invention, in the recycling step, the regenerated catalyst and/or the activated catalyst are recycled to the hydrogenation step. Herein, the recycling is preferably performed in a lifting pipe.

According to one embodiment of the present invention, there exists at least one step of degassing the spent catalyst (referred to as hydrogenation degassing step) between the hydrogenation step and the regeneration step.

According to one embodiment of the present invention, in the case that the activation step exists, there exists at least one step of degassing the regenerated catalyst (referred to as first regeneration degassing step) between the regeneration step and the activation step, optionally there exists at least one step of degassing the activated catalyst (referred to as activation degassing step) between the activation step and the recycling step, and optionally there exists at least one step of degassing the regenerated catalyst (referred to as second regeneration degassing step) between the regeneration step and the recycling step.

According to one embodiment of the present invention, in the case that the activation step is absent, there exists at least one step of degassing the regenerated catalyst (referred to as third regeneration degassing step) between the regeneration step and the recycling step.

According to one embodiment of the present invention, assuming the average mass flowrate (the unit is kg/h) of the spent catalyst being transported from the hydrogenation step to the hydrogenation degassing step is A1, the average mass flowrate (the unit is kg/h) of the spent catalyst being transported from the hydrogenation degassing step to the regeneration step is B1, the average mass flowrate (the unit is kg/h) of the regenerated catalyst being transported from the regeneration step to the first regeneration degassing step is A2, the average mass flowrate (the unit is kg/h) of the regenerated catalyst being transported from the first regeneration degassing step to the activation step is B2, the average mass flowrate (the unit is kg/h) of the activated catalyst being transported from the activation step to the activation degassing step is A3, the average mass flowrate (the unit is kg/h) of the activated catalyst being transported from the activation degassing step to the recycling step is B3, the average mass flowrate (the unit is kg/h) of the regenerated catalyst being transported from the regeneration step to the second regeneration degassing step is A4, the average mass flowrate (the unit is kg/h) of the regenerated catalyst being transported from the second regeneration degassing step to the recycling step is B4, the average mass flowrate (the unit is kg/h) of the regenerated catalyst being transported from the regeneration step to the third regeneration degassing step is A5, the average mass flowrate (the unit is kg/h) of the regenerated catalyst being transported from the third regeneration degassing step to the recycling step is B5, the average mass flowrate (the unit is kg/h) of the regenerated catalyst or the activated catalyst being transported from the recycling step to the hydrogenation step is A6, then at least one (preferably all) of A1 to A6 and B1 to B5 is 5-100 kg/h, preferably 10-30 kg/h. Herein, the so-called average mass flowrate refers to the mass of the fluid (such as catalyst) passing through the cross section of the transportation pipeline per unit time. The average mass flowrate can be calculated by the equation $$G_s = M \Big/ \left(t \cdot \frac{2T}{4} d^2\right),$$

where Gs is the average mass flowrate, a bypass is set at an arbitrary point of the pipeline, and a part of the catalyst particles is released during a period of time and collected, and the released amount of the catalyst particles is weighed and recorded as M (the unit is kg), the period time for releasing the catalyst particles is recorded as t (the unit is s), and the diameter of the pipeline at this point is recorded as d (the unit is m).

According to one embodiment of the present invention, assuming the particle volume fraction (the unit is %) in the transportation pipeline of the spent catalyst being transported from the hydrogenation step to the hydrogenation degassing step is C1, the particle volume fraction (the unit is %) in the transportation pipeline of the spent catalyst being transported from the hydrogenation degassing step to the regeneration step is D1, the particle volume fraction (the unit is %) in the transportation pipeline of the regenerated catalyst being transported from the regeneration step to the first regeneration degassing step is C2, the particle volume fraction (the unit is %) in the transportation pipeline of the regenerated catalyst being transported from the first regeneration degassing step to the activation step is D2, the particle volume fraction (the unit is %) in the transportation pipeline of the activated catalyst being transported from the activation step to the activation degassing step is C3, the particle volume fraction (the unit is %) in the transportation pipeline of the activated catalyst being transported from the activation degassing step to the recycling step is D3, the particle volume fraction (the unit is %) in the transportation pipeline of the regenerated catalyst being transported from the regeneration step to the second regeneration degassing step is C4, the particle volume fraction (the unit is %) in the transportation pipeline of the regenerated catalyst being transported from the second regeneration degassing step to the recycling step is D4, the particle volume fraction (the unit is %) in the transportation pipeline of the regenerated catalyst being transported from the regeneration step to the third regeneration degassing step is C5, the particle volume fraction (the unit is %) in the transportation pipeline of the regenerated catalyst being transported from the third regeneration degassing step to the recycling step is D5, the particle volume fraction (the unit is %) in the transportation pipeline of the regenerated catalyst or the activated catalyst being transported from the recycling step to the hydrogenation step is C6, then at least one (preferably all) of C1 to C6 and D1 to D5 is 0.1-15%, preferably 0.5-5%. Herein, the so-called particle volume fraction refers to the ratio of the volume of the particle phase to the total volume in the gas-solid two-phase mixture per unit volume. The particle volume fraction can be calculated by the equation $$\frac{\Delta P}{\Delta z} \approx [\rho_P(1-\varepsilon)+\rho\varepsilon]g,$$

wherein ΔP is the difference (the unit is Pa) between the pressure (gauge pressure) at Δz/2 below the position and the pressure (gauge pressure) at Δz/2 above the position, Δz is the distance (the unit is m) between the point at Δz/2 below the position and the point at Δz/2 above the position, $\rho_P$ is the particle density (the unit is $kg/m^3$) of the solid particles, ρ is the density (the unit is $kg/m^3$) of the gas, 1-ε is the particle volume fraction, ε is the gas volume fraction, the sum of the particle volume fraction and the gas volume fraction is 1, g is the absolute value of the gravity acceleration (generally taking 9.8 $m/s^2$).

According to one embodiment of the present invention, the superficial gas velocity of the hydrogenation step is generally 0.2-0.8 m/s, preferably 0.3-0.6 m/s, the molar ratio of hydrogen gas to the reaction raw material (for example nitrobenzene) is 6-21.

According to one embodiment of the present invention, the hydrogenation step has a reaction temperature (generally referring to the average reaction temperature in the dense phase reaction zone) of 220-280° C. and a reaction pressure (generally referring to the pressure in the dense phase reaction zone) of 0.05-1 MPa (gauge pressure). In addition, the temperature in the vicinity of the gas distributor 2 is generally controlled at 320° C. or less.

According to one embodiment of the present invention, the reaction conditions of the regeneration step comprise: in the presence of oxygen-containing gas (for example air or oxygen gas), the superficial gas velocity is 0.1-0.6 m/s, preferably 0.2-0.4 m/s.

According to one embodiment of the present invention, the regeneration step has a reaction temperature of 350-450° C. and a reaction pressure of 0.05-1 MPa (gauge pressure).

According to one embodiment of the present invention, the reaction conditions of the activation step comprise: in the presence of hydrogen gas, the superficial gas velocity is 0.1-0.6 m/s, the reaction temperature is 200-250° C., the reaction pressure is 0.05-1 MPa (gauge pressure).

According to one embodiment of the present invention, the hydrogenation reactor has a dimensionless particle diameter in the range of 1-60, and a dimensionless gas velocity in the range of 0.05-7.

According to one embodiment of the present invention, the regeneration reactor has a dimensionless particle diameter in the range of 1-40 and a dimensionless gas velocity in the range of 0.05-5.

According to one embodiment of the present invention, the activation reactor has a dimensionless particle diameter in the range of 1-30 and a dimensionless gas velocity in the range of 0.05-5.

According to one embodiment of the present invention, the dimensionless particle diameter of the hydrogenation reactor is in the range of 1-60, the dimensionless particle diameter of the regeneration reactor is in the range of 1-40, and the dimensionless particle diameter of the activation reactor is in the range of 1-30.

In the context of the present invention, the dimensionless particle diameter and the dimensionless gas velocity are respectively determined by the following two equations:

$$\text{Dimensionless particle diameter} = \text{Average particle diameter} \times [(\text{Gas density} \times \text{Gas-solid density difference} \times g)/(\text{Gas kinetic viscosity})^2]^{1/3},$$

$$\text{Dimensionless particle diameter} = \text{Average particle diameter} \times \sqrt[3]{\frac{\text{Gas density} \times \text{Gas} - \text{solid density difference} \times g}{\text{Gas kinetic viscosity}^2}},$$

$$\text{Dimensionless gas velocity} = \text{Superficial gas velocity} \times \sqrt[3]{\frac{\text{Gas density}^2}{\text{Gas}-\text{solid density difference} \times \text{Gas kinetic viscosity} \times g}},$$

In these equations, the average particle diameter is the volume average particle diameter (the unit is m) of solid particles in the reactor, the gas density is the density (the unit is $kg/m^3$) of the gas in the reactor, the gas-solid density difference is the difference of the density (the unit is $kg/m^3$) of solid particles minus the density (the unit is $kg/m^3$) of the gas in the reactor, the gas kinetic viscosity is the kinetic viscosity (the unit is Pa·s) of the gas in the reactor, the superficial gas velocity is the mean flow rate (the unit is m/s) of the gas passing through the reactor, and g is the absolute value of the gravity acceleration (9.8 $m/s^2$). Herein, the volume-average particle diameter can be obtained by the analysis of the sampled solid catalyst particles with a particle-size analyzer.

According to one embodiment of the present invention, the hydrogenation reaction process further comprises a step of transporting a supplement hydrogenation catalyst to at least one of the hydrogenation step, the regeneration step, the optional activation step and the recycling step, and preferably comprises a step of transporting a supplement hydrogenation catalyst to the activation step (referred to as catalyst supplement step).

According to one embodiment of the present invention, in the catalyst supplement step, the ratio of the average mass flowrate of the supplement hydrogenation catalyst being transported to the hydrogenation catalyst inventory in the hydrogenation reactor (the unit is kg) is 0-10 $h^{-1}$ (preferably 0.00002-0.001 $h^{-1}$). Herein, the hydrogenation catalyst inventory in the hydrogenation reactor can be calculated based on the bed pressure drop (the unit is Pa) and the reactor area (the unit is $m^2$) in the hydrogenation reactor.

According to one embodiment of the present invention, the hydrogenation reactor is a fluidized bed reactor. The fluidized bed reactor comprise a dense phase reaction zone (4), at least one dynamic pressure measuring point is mounted on the side wall of the dense phase reaction zone (4) to measure the instantaneous pressure fluctuation in the dense phase reaction zone (4). When the standard deviation of the instantaneous pressure fluctuation is greater than 600 Pa (preferably greater than 1500 Pa), the catalyst supplement step is initiated, that is to say the supplement hydrogenation catalyst is transported to at least one of the hydrogenation step, the regeneration step, the optional activation step and the recycling step, especially the supplement hydrogenation catalyst is transported to the activation step. Herein, preferably, the response frequency of said at least one dynamic pressure measuring point is not less than 100 Hz. In addition, the instantaneous pressure P at any time is resolved into the sum of the average value p and the fluctuation value p', that is, $$P_i = \overline{P} + P',$$

the standard deviation Sd at any measuring point is $$Sd = \sqrt{\frac{1}{N}\sum_{i=1}^{N}(P_i - \overline{P})^2},$$

and N is the number of the sampled data.

According to one embodiment of the present invention, the hydrogenation reactor is a fluidized bed reactor, the fluidized bed reactor comprise a dense phase reaction zone (4), when the catalyst particles having a particle diameter of less than 100 μm comprise greater than 3 wt % (preferably greater than 5 wt %) by mass percent of all catalyst particles in the dense phase reaction zone (4), the catalyst supplement step is initiated, that is to say the supplement hydrogenation catalyst is transported to at least one of the hydrogenation step, the regeneration step, the optional activation step and the recycling step, especially the supplement hydrogenation catalyst is transported to the activation step. Herein, the mass percent of the catalyst particles having a particle diameter of less than 100 μm relative to all catalyst particles is calculated by random sampling and then measurement by a particle size analyzer.

According to one embodiment of the present invention, as the supplement hydrogenation catalyst, any catalyst used in the art for the hydrogenation reaction of the nitro compound can be enumerated, and at least one selected from a copper-based loaded catalyst, a nickel-based loaded catalyst and a noble metal-based loaded catalyst, more especially a copper-based loaded catalyst can be particularly enumerated. Herein, for the copper-based loaded catalyst, copper is generally used as the main active component, and the support is generally alumina or silica.

According to one embodiment of the present invention, the average particle diameter of the supplement hydrogenation catalyst is generally 5-150 μm, preferably 20-70 μm. Herein, for example, the average particle diameter can be obtained by the analysis of the sampled solid catalyst particles with a particle-size analyzer.

According to one embodiment of the present invention, as the hydrogenation catalyst, any catalyst used in the art for the hydrogenation reaction of the nitro compound can be enumerated, and at least one selected from a copper-based loaded catalyst, a nickel-based loaded catalyst and a noble metal-based loaded catalyst, more especially a copper-based loaded catalyst can be particularly enumerated. Herein, for the copper-based loaded catalyst, copper is generally used as the main active component, and the support is generally alumina or silica.

According to one embodiment of the present invention, the average particle diameter of the hydrogenation catalyst is generally 30-800 μm, preferably 40-500 μm or 50-600 μm. Preferably, in the hydrogenation catalyst, the catalyst particles having a particle diameter of less than 80 μm comprises not less than 2 wt %, preferably 5-15 wt % by mass percent of all catalyst particles. For example, the average particle diameter can be obtained by the analysis of the sampled solid catalyst particles with a particle-size analyzer.

According to one embodiment of the present invention, the nitro compound is selected from at least one of the compounds represented by the following formula (1), preferably nitrobenzene.

$$R—NO_2 \tag{1}$$

According to the present invention, in the structural formula (1), R is an optionally substituted $C_{2-20}$ straight, branched or cyclic hydrocarbyl, preferably an optionally substituted $C_{4-20}$ cyclic hydrocarbyl, especially an optionally substituted $C_{6-20}$ aryl, more especially an optionally substituted phenyl or phenyl.

According to one embodiment of the present invention, it also relates to a hydrogenation reaction apparatus of the nitro compound, comprising a hydrogenation reactor, a regeneration reactor, an activation reactor and a recycling unit. Herein, the hydrogenation reaction apparatus is particularly designed to implement the nitro compound hydrogenation reaction process of the present invention. In view of this, for the contents or items that are not detailed hereinafter, the contents or items described as before in the present description for the nitro compound hydrogenation reaction process can be directly applied, and no detail will be provided herein. In addition, the contents or items described hereinafter for the hydrogenation reaction apparatus of the nitro compound can also be applied to the nitro compound hydrogenation reaction process of the present invention.

According to one embodiment of the present invention, as the recycling unit, the lifting pipe can be particularly enumerated.

According to one embodiment of the present invention, the hydrogenation reactor is communicated with the regeneration reactor via at least one spent catalyst degasser through transportation pipelines, the regeneration reactor is communicated with the activation reactor via at least one regenerated catalyst degasser through transportation pipelines, the activation reactor is communicated with the recycling unit through transportation pipelines or communicated with the recycling unit via at least one activated catalyst degasser through transportation pipelines, the recycling unit is communicated with the hydrogenation reactor through transportation pipelines.

According to one embodiment of the present invention, the solid particle inventory (the unit is kg) of the hydrogenation reactor: the solid particle inventory (the unit is kg) of the regeneration reactor: the solid particle inventory (the unit is kg) of the activation reactor=(10-200):(0.1-20):(0.1-20), preferably the solid particle inventory (the unit is kg) of the hydrogenation reactor: the solid particle inventory (the unit is kg) of the regeneration reactor:solid particle inventory (the unit is kg) of the activation reactor=(20-100):(0.5-8):(0.5-8). Herein, the solid particle inventory can be calculated based on the bed pressure drop (the unit is Pa) and the reactor area (the unit is $m^2$) in the reactor. Specifically, for example, if the solid particle inventory in the hydrogenation reactor is 10-200 tons, the solid particle inventory in the regeneration reactor and the activation reactor corresponds to 0.1-20 tons, or if the solid particle inventory in the hydrogenation reactor is 20-100 tons, the solid particle inventory in the regeneration reactor and the activation reactor corresponds to 0.5-8 tons.

According to one embodiment of the present invention, the hydrogenation reactor has a height of generally 5-60 m, preferably 10-30 m and a diameter of generally 0.5-12 m, preferably 1-8 m.

According to one embodiment of the present invention, the regeneration reactor has a height of generally 1-15 m, preferably 3-6 m and a diameter of generally 0.1-3 m, preferably 0.3-1 m.

According to one embodiment of the present invention, the activation reactor has a height of generally 1-15 m, preferably 3-6 m, and a diameter of generally 0.1-3 m, preferably 0.3-1 m.

According to one embodiment of the present invention, the inner diameters of the aforementioned transportation pipelines are, identical to or different from each other, each independently 30-400 mm, preferably 50-300 mm.

According to one embodiment of the present invention, the operation conditions of the degassing steps or the degassers are not particularly limited, and those well known in the art can be directly applied. Specifically, for example, the operating temperature is generally 0-700° C., preferably 80-400° C.; the operating pressure is generally 0-3 MPaG, preferably 0.01-1 MPaG; the superficial velocity (absolute value) is generally 0.05-0.6 m/s, preferably 0.1-0.4 m/s; the degassing agent is generally gas or vapor or steam, especially at least one selected from nitrogen gas, water vapour, carbon dioxide, methane and argon gas, especially nitrogen gas.

According to one embodiment of the present invention, the degassers used in the degassing steps or the structural style of the degassers and the like are not particularly limited, those well known in the art can be directly applied. For example, degassing tanks having a chevron baffle or a disc-ring baffle can be specifically enumerated. These degassing tanks have a degassing efficiency of generally 80% or higher, preferably 90% or higher, more preferably 94% or higher.

With reference to FIG. 1, the nitro compound hydrogenation reaction process and the hydrogenation reaction apparatus will be specifically described. Specifically, the main equipments of the nitro compound hydrogenation reaction process and the hydrogenation reaction apparatus comprise: a fluidized bed reactor 3, a degassing tank for the spent catalyst 12, a regeneration reactor 13, a degassing tank for the catalyst to be activated 16, an activation reactor 19 and a lifting pipe 21, wherein in the fluidized bed reactor 3 are included a dense phase reaction zone 4 located in the lower section, a particle sputtering transition zone 5 located in the middle section and a dilute-phase zone 7 located in the upper section, the degassing tank for the spent catalyst 12 is communicated with the fluidized bed reactor 3 and the regeneration reactor 13 respectively, the degassing tank for the catalyst to be activated 16 is communicated with the regeneration reactor 13 and the activation reactor 19 respectively, the lifting pipe 21 is communicated with the activation reactor 19 and the fluidized bed reactor 3 respectively. In the activation reactor 19 are provided a supplement fine particle feed inlet 22 and a supplement fresh catalyst feed inlet 23. Herein, in the fluidized bed reactor 3 are provided a gas distributor 2, a heat-exchanging pipe 11 and a cyclone separator 9.

According to one embodiment of the present invention, in the nitro compound hydrogenation reaction process and the hydrogenation reaction apparatus, vaporized nitrobenzene and hydrogen gas as raw material are introduced into a gas chamber, then into the fluidized bed reactor 3 through the gas distributor 2 to push the catalyst in the reactor to be fluidized, then react in the dense phase reaction zone 4 to produce an aniline product, a part of the gas phase forms bubbles, the particle sputtering occurs at the top of the dense phase reaction zone 4 to form a particle sputtering transition zone 5, the particles enter the dilute-phase zone 7 to be separated with a cyclone separator 9 and return to the dense phase reaction zone 4, the crude product gas 8 flows out of the fluidized bed reactor 3 and is sent into the subsequent separation section. After the catalyst is partly coked in the reaction, the coked catalyst is degassed in the degassing tank for the spent catalyst 12, and introduced into the regeneration reactor 13, to which the oxygen is introduced, the catalyst is regenerated by carbon burning. The regenerated catalyst is then introduced into the degassing tank for the catalyst to be activated 16 and degassed, and then introduced into the activation reactor 19, mixed with the supplement fine particles in the supplement fine particle feed inlet 22 used to optimize the fluidization quality in the dense phase reaction zone 4, and the fresh catalysts in the supplement fresh catalyst feed inlet 23 for supplementing the loss in the fluidized bed reactor 3, hydrogen gas is introduced to perform the activation, and the activated catalyst is introduced into the lifting pipe 21, and lifted up to return to the fluidized bed reactor 3 to proceed with the catalysis.

EXAMPLES

The present invention will be described in further detail below by way of examples and comparative examples, but the present invention is not limited to the following examples.

Example 1

The apparatus for producing aniline by the hydrogenation of nitrobenzene as shown in FIG. 1 was used, the fluidized bed reactor had a diameter of 45 mm. The solid particle reserve (the unit is kg) of the hydrogenation reactor:the solid particle reserve (the unit is kg) of the regeneration reactor: the solid particle reserve (the unit is kg) of the activation reactor=40:3:3. The height (the unit is m) of the hydrogenation reactor:the height (the unit is m) of the regeneration reactor:the height (the unit is m) of the activation reactor=5:1:1. The diameter (the unit is m) of the hydrogenation reactor:the diameter (the unit is m) of the regeneration reactor:the diameter (the unit is m) of the activation reactor=4:1:1.

The average mass flowrates for the transportation in the pipelines (A1-A6 and B1-B5) were all 13 kg/h, and for the particle volume fractions for the pipelines (C1-C6 and D1-D5), C1-C5 were 0.9%, C6 was 0.6%, D1-D5 were 1.2%. The catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa. The reaction conditions in the regenerator were as follows: the superficial gas velocity was 0.3 m/s, the average regeneration temperature was 410° C.; the reaction conditions in the activator were as follows: the superficial gas velocity was 0.3 m/s, the average activation temperature was 220° C.

The ratio of the average mass flowrate of the supplement hydrogenation catalyst being transported to the hydrogenation catalyst inventory in the hydrogenation reactor was 0.00005 kg/h, the dimensionless particle diameter in the fluidized bed reactor was 10, the dimensionless gas velocity in the fluidized bed reactor was 0.1, the dimensionless particle diameter in the regenerator was 8, the dimensionless gas velocity in the regenerator was 0.15, the particle diameter in the activator dimensionless was 8, the dimensionless gas velocity in the activator was 0.15, the standard deviation value of the pressure pulsation at any point of the bed layer of the dense phase reaction zone maintained by supplementing fine particles was 500 Pa.

The expansion coefficient of the dense phase reaction zone (the expansion coefficient=the height of the dense phase reaction zone/the height of the static bed, the fluidization quality was generally represented by the expansion coefficient, in general, the larger the expansion coefficient was, the better the fluidization quality was) was 1.64, the maximum temperature difference at any part in the reaction zone was 7.1° C., the carbon deposition content when the reaction time was 90 minutes under the high space velocity could be controlled at no greater than 0.7%, and the results were detailed in Table 1.

Example 2

The apparatus for producing aniline by the hydrogenation of nitrobenzene as shown in FIG. 1 was used, the fluidized bed reactor had a diameter of 45 mm. The solid particle inventory (the unit is kg) of the hydrogenation reactor:the solid particle inventory (the unit is kg) of the regeneration reactor:the solid particle inventory (the unit is kg) of the activation reactor=40:3:3. The height (the unit is m) of the hydrogenation reactor:the height (the unit is m) of the regeneration reactor:the height (the unit is m) of the activation reactor=5:1:1. The diameter (the unit is m) of the hydrogenation reactor:the diameter (the unit is m) of the regeneration reactor:the diameter (the unit is m) of the activation reactor=4:1:1.

The average mass flowrates for the transportation in the pipelines (A1-A6 and B1-B5) were all 13 kg/h, and for the particle volume fractions for the pipelines (C1-C6 and D1-D5), C1-C5 were 0.9%, C6 was 0.6%, D1-D5 were 1.2%. The catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa. The reaction conditions in the regenerator were as follows: the superficial gas velocity was 0.3 m/s, the average regeneration temperature was 410° C.; the reaction conditions in the activator were as follows: the superficial gas velocity was 0.3 m/s, the average activation temperature was 220° C.

The ratio of the average mass flowrate of the supplement hydrogenation catalyst being transported to the hydrogenation catalyst inventory in the hydrogenation reactor was 0.001 kg/h, the dimensionless particle diameter in the fluidized bed reactor was 10, the dimensionless gas velocity in the fluidized bed reactor was 0.1, the dimensionless particle diameter in the regenerator was 8, the dimensionless gas velocity in the regenerator was 0.15, the particle diameter in the activator dimensionless was 8, the dimensionless gas velocity in the activator was 0.15, the standard deviation value of the pressure pulsation at any point of the bed layer of the dense phase reaction zone maintained by supplementing fine particles was 500 Pa.

The expansion coefficient of the dense phase reaction zone was 1.58, the maximum temperature difference at any part in the reaction zone was 8.2° C., the carbon deposition content when the reaction time was 90 minutes under the high space velocity could be controlled at no greater than 0.51%, and the results were detailed in Table 1.

Example 3

The apparatus for producing aniline by the hydrogenation of nitrobenzene as shown in FIG. 1 was used, the fluidized bed reactor had a diameter of 45 mm. The solid particle inventory (the unit is kg) of the hydrogenation reactor:the solid particle inventory (the unit is kg) of the regeneration reactor:the solid particle inventory (the unit is kg) of the activation reactor=40:3:3.

The height (the unit is m) of the hydrogenation reactor:the height (the unit is m) of the regeneration reactor:the height (the unit is m) of the activation reactor=5:1:1. The diameter (the unit is m) of the hydrogenation reactor:the diameter (the unit is m) of the regeneration reactor:the diameter (the unit is m) of the activation reactor=4:1:1.

The average mass flowrates for the transportation in the pipelines (A1-A6 and B1-B5) were all 13 kg/h, and for the particle volume fractions for the pipelines (C1-C6 and D1-D5), C1-C5 were 0.9%, C6 was 0.6%, D1-D5 were 1.2%. The catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa. The reaction conditions in the regenerator were as follows: the superficial gas velocity was 0.3 m/s, the average regeneration temperature was 410° C.; the reaction conditions in the activator were as follows: the superficial gas velocity was 0.3 m/s, the average activation temperature was 220° C.

The ratio of the average mass flowrate of the supplement hydrogenation catalyst being transported to the hydrogenation catalyst inventory in the hydrogenation reactor was 0.00002 kg/h, the dimensionless particle diameter in the fluidized bed reactor was 10, the dimensionless gas velocity in the fluidized bed reactor was 0.1, the dimensionless particle diameter in the regenerator was 8, the dimensionless gas velocity in the regenerator was 0.15, the particle diameter in the activator dimensionless was 8, the dimensionless gas velocity in the activator was 0.15, the standard deviation value of the pressure pulsation at any point of the bed layer of the dense phase reaction zone maintained by supplementing fine particles was 500 Pa.

The expansion coefficient of the dense phase reaction zone was 1.61, the maximum temperature difference at any part in the reaction zone was 7.3° C., the carbon deposition content when the reaction time was 90 minutes under the high space velocity could be controlled at no greater than 0.55%, and the results were detailed in Table 1.

Example 4

The apparatus for producing aniline by the hydrogenation of nitrobenzene as shown in FIG. 1 was used, the fluidized bed reactor had a diameter of 45 mm. The solid particle inventory (the unit is kg) of the hydrogenation reactor:the solid particle inventory (the unit is kg) of the regeneration reactor:the solid particle inventory (the unit is kg) of the activation reactor=40:3:3. The height (the unit is m) of the hydrogenation reactor:the height (the unit is m) of the regeneration reactor:the height (the unit is m) of the activation reactor=5:1:1. The diameter (the unit is m) of the hydrogenation reactor:the diameter (the unit is m) of the regeneration reactor:the diameter (the unit is m) of the activation reactor=4:1:1.

The average mass flowrates for the transportation in the pipelines (A1-A6 and B1-B5) were all 13 kg/h, and for the particle volume fractions for the pipelines (C1-C6 and D1-D5), C1-C5 were 0.9%, C6 was 0.6%, D1-D5 were 1.2%. The catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa. The reaction conditions in the regenerator were as follows: the superficial gas velocity was 0.3 m/s, the average regeneration temperature was 410° C.; the reaction conditions in the activator were as follows: the superficial gas velocity was 0.3 m/s, the average activation temperature was 220° C.

The ratio of the average mass flowrate of the supplement hydrogenation catalyst being transported to the hydrogenation catalyst inventory in the hydrogenation reactor was 0.00005 kg/h, the dimensionless particle diameter in the fluidized bed reactor was 60, the dimensionless gas velocity in the fluidized bed reactor was 0.1, the dimensionless particle diameter in the regenerator was 8, the dimensionless gas velocity in the regenerator was 0.15, the particle diameter in the activator dimensionless was 8, the dimensionless gas velocity in the activator was 0.15, the standard deviation value of the pressure pulsation at any point of the bed layer of the dense phase reaction zone maintained by supplementing fine particles was 500 Pa.

The expansion coefficient of the dense phase reaction zone was 1.56, the maximum temperature difference at any part in the reaction zone was 7.5° C., the carbon deposition content when the reaction time was 90 minutes under the high space velocity could be controlled at no greater than 0.58%, and the results were detailed in Table 1.

Example 5

The apparatus for producing aniline by the hydrogenation of nitrobenzene as shown in FIG. 1 was used, the fluidized bed reactor had a diameter of 45 mm. The solid particle inventory (the unit is kg) of the hydrogenation reactor:the solid particle inventory (the unit is kg) of the regeneration reactor:the solid particle inventory (the unit is kg) of the activation reactor=40:3:3. The height (the unit is m) of the hydrogenation reactor:the height (the unit is m) of the regeneration reactor:the height (the unit is m) of the activation reactor=5:1:1. The diameter (the unit is m) of the hydrogenation reactor:the diameter (the unit is m) of the regeneration reactor:the diameter (the unit is m) of the activation reactor=4:1:1.

The average mass flowrates for the transportation in the pipelines (A1-A6 and B1-B5) were all 13 kg/h, and for the particle volume fractions for the pipelines (C1-C6 and D1-D5), C1-C5 were 0.9%, C6 was 0.6%, D1-D5 were 1.2%. The catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa. The reaction conditions in the regenerator were as follows: the superficial gas velocity was 0.3 m/s, the average regeneration temperature was 410° C.; the reaction conditions in the activator were as follows: the superficial gas velocity was 0.3 m/s, the average activation temperature was 220° C.

The ratio of the average mass flowrate of the supplement hydrogenation catalyst being transported to the hydrogenation catalyst inventory in the hydrogenation reactor was 0.00005 kg/h, the dimensionless particle diameter in the fluidized bed reactor was 1, the dimensionless gas velocity in the fluidized bed reactor was 0.1, the dimensionless particle diameter in the regenerator was 8, the dimensionless gas velocity in the regenerator was 0.15, the particle diameter in the activator dimensionless was 8, the dimensionless gas velocity in the activator was 0.15, the standard deviation value of the pressure pulsation at any point of the bed layer of the dense phase reaction zone maintained by supplementing fine particles was 500 Pa.

The expansion coefficient of the dense phase reaction zone was 1.55, the maximum temperature difference at any part in the reaction zone was 7.5° C., the carbon deposition content when the reaction time was 90 minutes under the high space velocity could be controlled at no greater than 0.76%, and the results were detailed in Table 1.

Example 6

The apparatus for producing aniline by the hydrogenation of nitrobenzene as shown in FIG. 1 was used, the fluidized bed reactor had a diameter of 45 mm. The solid particle inventory (the unit is kg) of the hydrogenation reactor:the solid particle inventory (the unit is kg) of the regeneration reactor:the solid particle inventory (the unit is kg) of the activation reactor=40:3:3.

The height (the unit is m) of the hydrogenation reactor:the height (the unit is m) of the regeneration reactor:the height (the unit is m) of the activation reactor=5:1:1. The diameter (the unit is m) of the hydrogenation reactor:the diameter (the unit is m) of the regeneration reactor:the diameter (the unit is m) of the activation reactor=4:1:1.

The average mass flowrates for the transportation in the pipelines (A1-A6 and B1-B5) were all 13 kg/h, and for the particle volume fractions for the pipelines (C1-C6 and D1-D5), C1-C5 were 0.9%, C6 was 0.6%, D1-D5 were 1.2%. The catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa. The reaction conditions in the regenerator were as follows: the superficial gas velocity was 0.3 m/s, the average regeneration temperature was 410° C.; the reaction conditions in the activator were as follows: the superficial gas velocity was 0.3 m/s, the average activation temperature was 220° C.

The ratio of the average mass flowrate of the supplement hydrogenation catalyst being transported to the hydrogenation catalyst inventory in the hydrogenation reactor was 0.00005 kg/h, the dimensionless particle diameter in the fluidized bed reactor was 10, the dimensionless gas velocity in the fluidized bed reactor was 0.05, the dimensionless particle diameter in the regenerator was 8, the dimensionless gas velocity in the regenerator was 0.15, the particle diameter in the activator dimensionless was 8, the dimensionless gas velocity in the activator was 0.15, the standard deviation value of the pressure pulsation at any point of the bed layer of the dense phase reaction zone maintained by supplementing fine particles was 500 Pa.

The expansion coefficient of the dense phase reaction zone was 1.61, the maximum temperature difference at any part in the reaction zone was 7.3° C., the carbon deposition content when the reaction time was 90 minutes under the high space velocity could be controlled at no greater than 0.72%, and the results were detailed in Table 2.

Example 7

The apparatus for producing aniline by the hydrogenation of nitrobenzene as shown in FIG. 1 was used, the fluidized bed reactor had a diameter of 45 mm. The solid particle inventory (the unit is kg) of the hydrogenation reactor:the solid particle inventory (the unit is kg) of the regeneration reactor:the solid particle inventory (the unit is kg) of the activation reactor=40:3:3. The height (the unit is m) of the hydrogenation reactor:the height (the unit is m) of the regeneration reactor:the height (the unit is m) of the activation reactor=5:1:1. The diameter (the unit is m) of the hydrogenation reactor:the diameter (the unit is m) of the regeneration reactor:the diameter (the unit is m) of the activation reactor=4:1:1.

The average mass flowrates for the transportation in the pipelines (A1-A6 and B1-B5) were all 13 kg/h, and for the particle volume fractions for the pipelines (C1-C6 and D1-D5), C1-C5 were 0.9%, C6 was 0.6%, D1-D5 were 1.2%. The catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa. The reaction conditions in the regenerator were as follows: the superficial gas velocity was 0.3 m/s, the average regeneration temperature was 410° C.; the reaction conditions in the activator were as follows: the superficial gas velocity was 0.3 m/s, the average activation temperature was 220° C.

The ratio of the average mass flowrate of the supplement hydrogenation catalyst being transported to the hydrogenation catalyst inventory in the hydrogenation reactor was 0.00005 kg/h, the dimensionless particle diameter in the fluidized bed reactor was 10, the dimensionless gas velocity in the fluidized bed reactor was 7, the dimensionless particle diameter in the regenerator was 8, the dimensionless gas velocity in the regenerator was 0.15, the particle diameter in the activator dimensionless was 8, the dimensionless gas velocity in the activator was 0.15, the standard deviation value of the pressure pulsation at any point of the bed layer of the dense phase reaction zone maintained by supplementing fine particles was 500 Pa.

The expansion coefficient of the dense phase reaction zone was 1.60, the maximum temperature difference at any part in the reaction zone was 7.3° C., the carbon deposition content when the reaction time was 90 minutes under the high space velocity could be controlled at no greater than 0.72%, and the results were detailed in Table 2.

Example 8

The apparatus for producing aniline by the hydrogenation of nitrobenzene as shown in FIG. 1 was used, the fluidized bed reactor had a diameter of 45 mm. The solid particle inventory (the unit is kg) of the hydrogenation reactor:the solid particle inventory (the unit is kg) of the regeneration reactor:the solid particle inventory (the unit is kg) of the activation reactor=40:3:3. The height (the unit is m) of the hydrogenation reactor:the height (the unit is m) of the regeneration reactor:the height (the unit is m) of the activation reactor=5:1:1. The diameter (the unit is m) of the hydrogenation reactor:the diameter (the unit is m) of the regeneration reactor:the diameter (the unit is m) of the activation reactor=4:1:1.

The average mass flowrates for the transportation in the pipelines (A1-A6 and B1-B5) were all 13 kg/h, and for the particle volume fractions for the pipelines (C1-C6 and D1-D5), C1-C5 were 0.9%, C6 was 0.6%, D1-D5 were 1.2%. The catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa. The reaction conditions in the regenerator were as follows: the superficial gas velocity was 0.3 m/s, the average regeneration temperature was 410° C.; the reaction conditions in the activator were as follows: the superficial gas velocity was 0.3 m/s, the average activation temperature was 220° C.

The ratio of the average mass flowrate of the supplement hydrogenation catalyst being transported to the hydrogenation catalyst inventory in the hydrogenation reactor was 0.00005 kg/h, the dimensionless particle diameter in the fluidized bed reactor was 10, the dimensionless gas velocity in the fluidized bed reactor was 0.1, the dimensionless particle diameter in the regenerator was 1, the dimensionless gas velocity in the regenerator was 0.05, the particle diameter in the activator dimensionless was 8, the dimensionless gas velocity in the activator was 0.15, the standard deviation value of the pressure pulsation at any point of the bed layer of the dense phase reaction zone maintained by supplementing fine particles was 500 Pa.

The expansion coefficient of the dense phase reaction zone was 1.59, the maximum temperature difference at any part in the reaction zone was 7.6° C., the carbon deposition content when the reaction time was 90 minutes under the high space velocity could be controlled at no greater than 0.74%, and the results were detailed in Table 2.

Example 9

The apparatus for producing aniline by the hydrogenation of nitrobenzene as shown in FIG. 1 was used, the fluidized bed reactor had a diameter of 45 mm. The solid particle inventory (the unit is kg) of the hydrogenation reactor:the solid particle inventory (the unit is kg) of the regeneration reactor:the solid particle inventory (the unit is kg) of the activation reactor=40:3:3. The height (the unit is m) of the hydrogenation reactor:the height (the unit is m) of the regeneration reactor:the height (the unit is m) of the activation reactor=5:1:1. The diameter (the unit is m) of the hydrogenation reactor:the diameter (the unit is m) of the regeneration reactor:the diameter (the unit is m) of the activation reactor=4:1:1.

The average mass flowrates for the transportation in the pipelines (A1-A6 and B1-B5) were all 13 kg/h, and for the particle volume fractions for the pipelines (C1-C6 and D1-D5), C1-C5 were 0.9%, C6 was 0.6%, D1-D5 were 1.2%. The catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa. The reaction conditions in the regenerator were as follows: the superficial gas velocity was 0.3 m/s, the average regeneration temperature was 410° C.; the reaction conditions in the activator were as follows: the superficial gas velocity was 0.3 m/s, the average activation temperature was 220° C.

The ratio of the average mass flowrate of the supplement hydrogenation catalyst being transported to the hydrogenation catalyst inventory in the hydrogenation reactor was 0.00005 kg/h, the dimensionless particle diameter in the fluidized bed reactor was 10, the dimensionless gas velocity in the fluidized bed reactor was 0.1, the dimensionless particle diameter in the regenerator was 36, the dimensionless gas velocity in the regenerator was 5, the particle diameter in the activator dimensionless was 8, the dimensionless gas velocity in the activator was 0.15, the standard deviation value of the pressure pulsation at any point of the bed layer of the dense phase reaction zone maintained by supplementing fine particles was 500 Pa.

The expansion coefficient of the dense phase reaction zone was 1.54, the maximum temperature difference at any part in the reaction zone was 8.0° C., the carbon deposition content when the reaction time was 90 minutes under the high space velocity could be controlled at no greater than 0.8%, and the results were detailed in Table 2.

Example 10

The apparatus for producing aniline by the hydrogenation of nitrobenzene as shown in FIG. 1 was used, the fluidized bed reactor had a diameter of 45 mm. The solid particle inventory (the unit is kg) of the hydrogenation reactor:the solid particle inventory (the unit is kg) of the regeneration reactor:the solid particle inventory (the unit is kg) of the activation reactor=40:3:3. The height (the unit is m) of the hydrogenation reactor:the height (the unit is m) of the regeneration reactor:the height (the unit is m) of the activation reactor=5:1:1. The diameter (the unit is m) of the hydrogenation reactor:the diameter (the unit is m) of the regeneration reactor:the diameter (the unit is m) of the activation reactor=4:1:1.

The average mass flowrates for the transportation in the pipelines (A1-A6 and B1-B5) were all 13 kg/h, and for the particle volume fractions for the pipelines (C1-C6 and D1-D5), C1-C5 were 0.9%, C6 was 0.6%, D1-D5 were 1.2%. The catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa. The reaction conditions in the regenerator were as follows: the superficial gas velocity was 0.3 m/s, the average regeneration temperature was 410° C.; the reaction conditions in the activator were as follows: the superficial gas velocity was 0.3 m/s, the average activation temperature was 220° C.

The ratio of the average mass flowrate of the supplement hydrogenation catalyst being transported to the hydrogenation catalyst inventory in the hydrogenation reactor was 0.00005 kg/h, the dimensionless particle diameter in the fluidized bed reactor was 10, the dimensionless gas velocity in the fluidized bed reactor was 0.1, the dimensionless particle diameter in the regenerator was 8, the dimensionless gas velocity in the regenerator was 0.15, the particle diameter in the activator dimensionless was 1, the dimensionless gas velocity in the activator was 0.05, the standard deviation value of the pressure pulsation at any point of the bed layer of the dense phase reaction zone maintained by supplementing fine particles was 500 Pa.

The expansion coefficient of the dense phase reaction zone was 1.59, the maximum temperature difference at any part in the reaction zone was 7.6° C., the carbon deposition content when the reaction time was 90 minutes under the high space velocity could be controlled at no greater than 0.76%, and the results were detailed in Table 2.

Example 11

The apparatus for producing aniline by the hydrogenation of nitrobenzene as shown in FIG. 1 was used, the fluidized bed reactor had a diameter of 45 mm. The solid particle inventory (the unit is kg) of the hydrogenation reactor:the solid particle inventory (the unit is kg) of the regeneration reactor:the solid particle inventory (the unit is kg) of the activation reactor=40:3:3. The height (the unit is m) of the hydrogenation reactor:the height (the unit is m) of the regeneration reactor:the height (the unit is m) of the activation reactor=5:1:1. The diameter (the unit is m) of the hydrogenation reactor:the diameter (the unit is m) of the regeneration reactor:the diameter (the unit is m) of the activation reactor=4:1:1.

The average mass flowrates for the transportation in the pipelines (A1-A6 and B1-B5) were all 13 kg/h, and for the particle volume fractions for the pipelines (C1-C6 and D1-D5), C1-C5 were 0.9%, C6 was 0.6%, D1-D5 were 1.2%. The catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa. The reaction conditions in the regenerator were as follows: the superficial gas velocity was 0.3 m/s, the average regeneration temperature was 410° C.; the reaction conditions in the activator were as follows: the superficial gas velocity was 0.3 m/s, the average activation temperature was 220° C.

The ratio of the average mass flowrate of the supplement hydrogenation catalyst being transported to the hydrogenation catalyst inventory in the hydrogenation reactor was 0.00005 kg/h, the dimensionless particle diameter in the fluidized bed reactor was 10, the dimensionless gas velocity in the fluidized bed reactor was 0.1, the dimensionless particle diameter in the regenerator was 8, the dimensionless gas velocity in the regenerator was 0.15, the particle diameter in the activator dimensionless was 25, the dimensionless gas velocity in the activator was 5, the standard deviation value of the pressure pulsation at any point of the bed layer of the dense phase reaction zone maintained by supplementing fine particles was 500 Pa.

The expansion coefficient of the dense phase reaction zone was 1.60, the maximum temperature difference at any part in the reaction zone was 7.4° C., the carbon deposition content when the reaction time was 90 minutes under the high space velocity could be controlled at no greater than 0.75%, and the results were detailed in Table 3.

Example 12

The apparatus for producing aniline by the hydrogenation of nitrobenzene as shown in FIG. 1 was used, the fluidized bed reactor had a diameter of 45 mm. The solid particle inventory (the unit is kg) of the hydrogenation reactor:the solid particle inventory (the unit is kg) of the regeneration reactor:the solid particle inventory (the unit is kg) of the activation reactor=40:3:3. The height (the unit is m) of the hydrogenation reactor:the height (the unit is m) of the regeneration reactor:the height (the unit is m) of the activation reactor=5:1:1. The diameter (the unit is m) of the hydrogenation reactor:the diameter (the unit is m) of the regeneration reactor:the diameter (the unit is m) of the activation reactor=4:1:1.

The average mass flowrates for the transportation in the pipelines (A1-A6 and B1-B5) were all 13 kg/h, and for the particle volume fractions for the pipelines (C1-C6 and D1-D5), C1-C5 were 0.9%, C6 was 0.6%, D1-D5 were 1.2%. The catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa. The reaction conditions in the regenerator were as follows: the superficial gas velocity was 0.3 m/s, the average regeneration temperature was 410° C.; the reaction conditions in the activator were as follows: the superficial gas velocity was 0.3 m/s, the average activation temperature was 220° C.

The ratio of the average mass flowrate of the supplement hydrogenation catalyst being transported to the hydrogenation catalyst inventory in the hydrogenation reactor was 0.00005 kg/h, the dimensionless particle diameter in the fluidized bed reactor was 10, the dimensionless gas velocity in the fluidized bed reactor was 0.1, the dimensionless particle diameter in the regenerator was 8, the dimensionless gas velocity in the regenerator was 0.15, the particle diameter in the activator dimensionless was 8, the dimensionless gas velocity in the activator was 0.15, the standard deviation value of the pressure pulsation at any point of the bed layer of the dense phase reaction zone maintained by supplementing fine particles was 700 Pa.

The expansion coefficient of the dense phase reaction zone was 1.62, the maximum temperature difference at any part in the reaction zone was 7.2° C., the carbon deposition content when the reaction time was 90 minutes under the high space velocity could be controlled at no greater than 0.7%, and the results were detailed in Table 3.

Example 13

The apparatus for producing aniline by the hydrogenation of nitrobenzene as shown in FIG. 1 was used, the fluidized bed reactor had a diameter of 45 mm. The solid particle inventory (the unit is kg) of the hydrogenation reactor:the solid particle inventory (the unit is kg) of the regeneration reactor:the solid particle inventory (the unit is kg) of the activation reactor=40:3:3. The height (the unit is m) of the hydrogenation reactor:the height (the unit is m) of the regeneration reactor:the height (the unit is m) of the activation reactor=5:1:1. The diameter (the unit is m) of the hydrogenation reactor:the diameter (the unit is m) of the regeneration reactor:the diameter (the unit is m) of the activation reactor=4:1:1.

The average mass flowrates for the transportation in the pipelines (A1-A6 and B1-B5) were all 13 kg/h, and for the particle volume fractions for the pipelines (C1-C6 and D1-D5), C1-C5 were 0.9%, C6 was 0.6%, D1-D5 were 1.2%. The catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa. The reaction conditions in the regenerator were as follows: the superficial gas velocity was 0.3 m/s, the average regeneration temperature was 410° C.; the reaction conditions in the activator were as follows: the superficial gas velocity was 0.3 m/s, the average activation temperature was 220° C.

The ratio of the average mass flowrate of the supplement hydrogenation catalyst being transported to the hydrogenation catalyst inventory in the hydrogenation reactor was 0.00005 kg/h, the dimensionless particle diameter in the fluidized bed reactor was 10, the dimensionless gas velocity in the fluidized bed reactor was 0.1, the dimensionless particle diameter in the regenerator was 8, the dimensionless gas velocity in the regenerator was 0.15, the particle diameter in the activator dimensionless was 8, the dimensionless gas velocity in the activator was 0.15, the standard deviation value of the pressure pulsation at any point of the bed layer of the dense phase reaction zone maintained by supplementing fine particles was 1500 Pa.

The expansion coefficient of the dense phase reaction zone was 1.52, the maximum temperature difference at any part in the reaction zone was 10.5° C., the carbon deposition content when the reaction time was 90 minutes under the high space velocity could be controlled at no greater than 0.7%, and the results were detailed in Table 3.

Example 14

The apparatus for producing aniline by the hydrogenation of nitrobenzene as shown in FIG. 1 was used, the fluidized bed reactor had a diameter of 45 mm. The solid particle inventory (the unit is kg) of the hydrogenation reactor:the solid particle inventory (the unit is kg) of the regeneration reactor:the solid particle inventory (the unit is kg) of the activation reactor=40:3:3. The height (the unit is m) of the hydrogenation reactor:the height (the unit is m) of the regeneration reactor:the height (the unit is m) of the activation reactor=5:1:1. The diameter (the unit is m) of the hydrogenation reactor:the diameter (the unit is m) of the regeneration reactor:the diameter (the unit is m) of the activation reactor=4:1:1.

The average mass flowrates for the transportation in the pipelines (A1-A6 and B1-B5) were all 7 kg/h, and for the particle volume fractions for the pipelines (C1-C6 and D1-D5), C1-C5 were 0.83%, C6 was 0.55%, D1-D5 were 1.06%. The catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa. The reaction conditions in the regenerator were as follows: the superficial gas velocity was 0.3 m/s, the average regeneration temperature was 410° C.; the reaction conditions in the activator were as follows: the superficial gas velocity was 0.3 m/s, the average activation temperature was 220° C.

The ratio of the average mass flowrate of the supplement hydrogenation catalyst being transported to the hydrogenation catalyst inventory in the hydrogenation reactor was 0.00005 kg/h, the dimensionless particle diameter in the fluidized bed reactor was 10, the dimensionless gas velocity in the fluidized bed reactor was 0.1, the dimensionless particle diameter in the regenerator was 8, the dimensionless gas velocity in the regenerator was 0.15, the particle diameter in the activator dimensionless was 8, the dimensionless gas velocity in the activator was 0.15, the standard deviation value of the pressure pulsation at any point of the bed layer of the dense phase reaction zone maintained by supplementing fine particles was 500 Pa.

The expansion coefficient of the dense phase reaction zone (the expansion coefficient=the height of the dense phase reaction zone/the height of the static bed, the fluidization quality was generally represented by the expansion coefficient, in general, the larger the expansion coefficient was, the better the fluidization quality was) was 1.62, the maximum temperature difference at any part in the reaction zone was 7.2° C., the carbon deposition content when the reaction time was 90 minutes under the high space velocity could be controlled at no greater than 0.93%, and the results were detailed in Table 3.

Example 15

The apparatus for producing aniline by the hydrogenation of nitrobenzene as shown in FIG. 1 was used, the fluidized bed reactor had a diameter of 45 mm. The solid particle inventory (the unit is kg) of the hydrogenation reactor:the solid particle inventory (the unit is kg) of the regeneration reactor:the solid particle inventory (the unit is kg) of the activation reactor=40:3:3. The height (the unit is m) of the hydrogenation reactor:the height (the unit is m) of the regeneration reactor:the height (the unit is m) of the activation reactor=5:1:1. The diameter (the unit is m) of the hydrogenation reactor:the diameter (the unit is m) of the regeneration reactor:the diameter (the unit is m) of the activation reactor=4:1:1.

The average mass flowrates for the transportation in the pipelines (A1-A6 and B1-B5) were all 26 kg/h, and for the particle volume fractions for the pipelines (C1-C6 and D1-D5), C1-C5 were 1.1%, C6 was 0.7%, D1-D5 were 1.5%. The catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa. The reaction conditions in the regenerator were as follows: the superficial gas velocity was 0.3 m/s, the average regeneration temperature was 410° C.; the reaction conditions in the activator were as follows: the superficial gas velocity was 0.3 m/s, the average activation temperature was 220° C.

The ratio of the average mass flowrate of the supplement hydrogenation catalyst being transported to the hydrogenation catalyst inventory in the hydrogenation reactor was 0.00005 kg/h, the dimensionless particle diameter in the fluidized bed reactor was 10, the dimensionless gas velocity in the fluidized bed reactor was 0.1, the dimensionless particle diameter in the regenerator was 8, the dimensionless gas velocity in the regenerator was 0.15, the particle diameter in the activator dimensionless was 8, the dimensionless gas velocity in the activator was 0.15, the standard deviation value of the pressure pulsation at any point of the bed layer of the dense phase reaction zone maintained by supplementing fine particles was 500 Pa.

The expansion coefficient of the dense phase reaction zone (the expansion coefficient=the height of the dense phase reaction zone/the height of the static bed, the fluidization quality was generally represented by the expansion coefficient, in general, the larger the expansion coefficient was, the better the fluidization quality was) was 1.67, the maximum temperature difference at any part in the reaction zone was 6.9° C., the carbon deposition content when the reaction time was 90 minutes under the high space velocity could be controlled at no greater than 0.47%, and the results were detailed in Table 3.

Example 16

The apparatus for producing aniline by the hydrogenation of nitrobenzene as shown in FIG. 1 was used, the fluidized bed reactor had a diameter of 45 mm. The solid particle inventory (the unit is kg) of the hydrogenation reactor:the solid particle inventory (the unit is kg) of the regeneration reactor:the solid particle inventory (the unit is kg) of the activation reactor=30:1:1.

The height (the unit is m) of the hydrogenation reactor:the height (the unit is m) of the regeneration reactor:the height (the unit is m) of the activation reactor=5:1:1. The diameter (the unit is m) of the hydrogenation reactor:the diameter (the unit is m) of the regeneration reactor:the diameter (the unit is m) of the activation reactor=4:1:1.

The average mass flowrates for the transportation in the pipelines (A1-A6 and B1-B5) were all 13 kg/h, and for the particle volume fractions for the pipelines (C1-C6 and D1-D5), C1-C5 were 0.9%, C6 was 0.6%, D1-D5 were 1.2%. The catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa. The reaction conditions in the regenerator were as follows: the superficial gas velocity was 0.3 m/s, the average regeneration temperature was 410° C.; the reaction conditions in the activator were as follows: the superficial gas velocity was 0.3 m/s, the average activation temperature was 220° C.

The ratio of the average mass flowrate of the supplement hydrogenation catalyst being transported to the hydrogenation catalyst inventory in the hydrogenation reactor was 0.00005 kg/h, the dimensionless particle diameter in the fluidized bed reactor was 10, the dimensionless gas velocity in the fluidized bed reactor was 0.1, the dimensionless particle diameter in the regenerator was 8, the dimensionless gas velocity in the regenerator was 0.15, the particle diameter in the activator dimensionless was 8, the dimensionless gas velocity in the activator was 0.15, the standard deviation value of the pressure pulsation at any point of the bed layer of the dense phase reaction zone maintained by supplementing fine particles was 500 Pa.

The expansion coefficient of the dense phase reaction zone (the expansion coefficient=the height of the dense phase reaction zone/the height of the static bed, the fluidization quality was generally represented by the expansion coefficient, in general, the larger the expansion coefficient was, the better the fluidization quality was) was 1.62, the maximum temperature difference at any part in the reaction zone was 7.2° C., the carbon deposition content when the reaction time was 90 minutes under the high space velocity could be controlled at no greater than 0.7%, and the results were detailed in Table 4.

Example 17

The apparatus for producing aniline by the hydrogenation of nitrobenzene as shown in FIG. 1 was used, the fluidized bed reactor had a diameter of 45 mm. The solid particle inventory (the unit is kg) of the hydrogenation reactor:the solid particle inventory (the unit is kg) of the regeneration reactor:the solid particle inventory (the unit is kg) of the activation reactor=40:3:3. The height (the unit is m) of the hydrogenation reactor:the height (the unit is m) of the regeneration reactor:the height (the unit is m) of the activation reactor=2:1:1. The diameter (the unit is m) of the hydrogenation reactor:the diameter (the unit is m) of the regeneration reactor:the diameter (the unit is m) of the activation reactor=4:1:1.

The average mass flowrates for the transportation in the pipelines (A1-A6 and B1-B5) were all 13 kg/h, and for the particle volume fractions for the pipelines (C1-C6 and D1-D5), C1-C5 were 0.9%, C6 was 0.6%, D1-D5 were 1.2%. The catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa. The reaction conditions in the regenerator were as follows: the superficial gas velocity was 0.3 m/s, the average regeneration temperature was 410° C.; the reaction conditions in the activator were as follows: the superficial gas velocity was 0.3 m/s, the average activation temperature was 220° C.

The ratio of the average mass flowrate of the supplement hydrogenation catalyst being transported to the hydrogenation catalyst inventory in the hydrogenation reactor was 0.00005 kg/h, the dimensionless particle diameter in the fluidized bed reactor was 10, the dimensionless gas velocity in the fluidized bed reactor was 0.1, the dimensionless particle diameter in the regenerator was 8, the dimensionless gas velocity in the regenerator was 0.15, the particle diameter in the activator dimensionless was 8, the dimensionless gas velocity in the activator was 0.15, the standard deviation value of the pressure pulsation at any point of the bed layer of the dense phase reaction zone maintained by supplementing fine particles was 500 Pa.

The expansion coefficient of the dense phase reaction zone (the expansion coefficient=the height of the dense phase reaction zone/the height of the static bed, the fluidization quality was generally represented by the expansion coefficient, in general, the larger the expansion coefficient was, the better the fluidization quality was) was 1.64, the maximum temperature difference at any part in the reaction zone was 7.2° C., the carbon deposition content when the reaction time was 90 minutes under the high space velocity could be controlled at no greater than 0.7%, and the results were detailed in Table 4.

Example 18

The apparatus for producing aniline by the hydrogenation of nitrobenzene as shown in FIG. 1 was used, the fluidized bed reactor had a diameter of 45 mm. The solid particle inventory (the unit is kg) of the hydrogenation reactor:the solid particle inventory (the unit is kg) of the regeneration reactor:the solid particle inventory (the unit is kg) of the activation reactor=40:3:3. The height (the unit is m) of the hydrogenation reactor:the height (the unit is m) of the regeneration reactor:the height (the unit is m) of the activation reactor=5:1:1. The diameter (the unit is m) of the hydrogenation reactor:the diameter (the unit is m) of the regeneration reactor:the diameter (the unit is m) of the activation reactor=6:1:1.

The average mass flowrates for the transportation in the pipelines (A1-A6 and B1-B5) were all 13 kg/h, and for the particle volume fractions for the pipelines (C1-C6 and D1-D5), C1-C5 were 0.9%, C6 was 0.6%, D1-D5 were 1.2%. The catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa. The reaction conditions in the regenerator were as follows: the superficial gas velocity was 0.3 m/s, the average regeneration temperature was 410° C.; the reaction conditions in the activator were as follows: the superficial gas velocity was 0.3 m/s, the average activation temperature was 220° C.

The ratio of the average mass flowrate of the supplement hydrogenation catalyst being transported to the hydrogenation catalyst inventory in the hydrogenation reactor was 0.00005 kg/h, the dimensionless particle diameter in the fluidized bed reactor was 10, the dimensionless gas velocity in the fluidized bed reactor was 0.1, the dimensionless particle diameter in the regenerator was 8, the dimensionless gas velocity in the regenerator was 0.15, the particle diameter in the activator dimensionless was 8, the dimensionless gas velocity in the activator was 0.15, the standard deviation value of the pressure pulsation at any point of the bed layer of the dense phase reaction zone maintained by supplementing fine particles was 500 Pa.

The expansion coefficient of the dense phase reaction zone (the expansion coefficient=the height of the dense phase reaction zone/the height of the static bed, the fluidization quality was generally represented by the expansion coefficient, in general, the larger the expansion coefficient was, the better the fluidization quality was) was 1.66, the maximum temperature difference at any part in the reaction zone was 7.0° C., the carbon deposition content when the reaction time was 90 minutes under the high space velocity could be controlled at no greater than 0.73%, and the results were detailed in Table 1.

Comparative Example 1

The apparatus for producing aniline by the hydrogenation of nitrobenzene as shown in FIG. 1 was used. The apparatus for producing aniline by the hydrogenation of nitrobenzene as shown in FIG. 1 was used, the fluidized bed reactor had a diameter of 45 mm. The solid particle inventory (the unit is kg) of the hydrogenation reactor:the solid particle inventory (the unit is kg) of the regeneration reactor:the solid particle inventory (the unit is kg) of the activation reactor=40:3:3. The height (the unit is m) of the hydrogenation reactor:the height (the unit is m) of the regeneration reactor: the height (the unit is m) of the activation reactor=5:1:1. The diameter (the unit is m) of the hydrogenation reactor:the diameter (the unit is m) of the regeneration reactor:the diameter (the unit is m) of the activation reactor=4:1:1.

The average mass flowrates for the transportation in the pipelines (A1-A6 and B1-B5) were all 7 kg/h, and for the particle volume fractions for the pipelines (C1-C6 and D1-D5), C1-C5 were 0.83%, C6 was 0.55%, D1-D5 were 1.06%. The catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa. The reaction conditions in the regenerator were as follows: the superficial gas velocity was 0.3 m/s, the average regeneration temperature was 410° C.; the reaction conditions in the activator were as follows: the superficial gas velocity was 0.3 m/s, the average activation temperature was 220° C.

The ratio of the average mass flowrate of the supplement hydrogenation catalyst being transported to the hydrogenation catalyst inventory in the hydrogenation reactor was 0.00005 kg/h, the dimensionless particle diameter in the fluidized bed reactor was 10, the dimensionless gas velocity in the fluidized bed reactor was 0.1, the dimensionless particle diameter in the regenerator was 8, the dimensionless gas velocity in the regenerator was 0.15, the particle diameter in the activator dimensionless was 8, the dimensionless gas velocity in the activator was 0.15, the supplement of the fine particle catalyst was controlled not according to the pressure pulsation in the reaction dense phase zone.

The expansion coefficient of the dense phase reaction zone was 1.46, the maximum temperature difference at any part in the reaction zone was 13.8° C., the carbon deposition content when the reaction time was 90 minutes under the high space velocity could be controlled at no greater than 0.7%, and the results were detailed in Table 4.

Comparative Example 2

The prior art fluidized bed reactor apparatus for producing aniline by the hydrogenation of nitrobenzene without a regenerator and an activator was used, and the supplement of the fine particle catalyst was controlled not according to the pressure pulsation in the reaction dense phase zone. The fluidized bed reactor had a diameter of 45 mm. The used catalyst was a metal loaded catalyst with copper as the main active component, the support was silica, the catalyst had an average particle diameter of 400 μm, and the content of particles lower than 100 μm was 5%. The reaction conditions in the fluidized bed reactor were as follows: the superficial gas velocity was 0.4 m/s, the molar ratio of hydrogen gas to nitrobenzene was 11, the average reaction temperature in the dense phase reaction zone was controlled at 240° C., the reaction pressure in the dense phase reaction zone was 0.1 MPa.

The expansion coefficient of the dense phase reaction zone was 1.38, the maximum temperature difference at any part in the reaction zone was 15.9° C., and the results were detailed in Table 4.

Obviously, the apparatus and the process of the present invention can solve the problems such as the poor fluidization quality of the coarse particles in the fluidized bed technology of the nitrobenzene hydrogenation to produce aniline, the uneven temperature distribution in the reaction zone were, the catalysts prone to coking and deactivation, the difficulty in the long-period run, the necessity for supplementing the catalyst and the like, and can be used in the industrial run for the nitrobenzene hydrogenation to produce aniline.

TABLE 1

| | Example 1 | Example 2 | Example 3 | Example 4 | Example 5 |
|---|---|---|---|---|---|
| Average mass flowrate (A1-A6 and B1-B5), kg/h | All 13 | All 13 | All 13 | All 13 | All 13 |
| Particle volume fractions for the pipelines (C1-C6 and D1-D5) | C1-C5 were 0.9%, C6 was 0.6%, D1-D5 were 1.2% | C1-C5 were 0.9%, C6 was 0.6%, D1-D5 were 1.2% | C1-C5 were 0.9%, C6 was 0.6%, D1-D5 were 1.2% | C1-C5 were 0.9%, C6 was 0.6%, D1-D5 were 1.2% | C1-C5 were 0.9%, C6 was 0.6%, D1-D5 were 1.2% |
| Ratio of the average mass flowrate of the supplement hydrogenation catalyst being transported to the hydrogenation catalyst inventory in the hydrogenation reactor, $h^{-1}$ | 0.00005 | 0.001 | 0.00002 | 0.00005 | 0.00005 |
| Dimensionless particle diameter in the fluidized bed reactor | 10 | 10 | 10 | 60 | 1 |
| dimensionless gas velocity in the fluidized bed reactor | 0.1 | 0.1 | 0.1 | 0.1 | 0.1 |
| Dimensionless particle diameter in the regenerator | 8 | 8 | 8 | 8 | 8 |
| Dimensionless gas velocity in the regenerator | 0.15 | 0.15 | 0.15 | 0.15 | 0.15 |
| Dimensionless particle diameter in the activator | 8 | 8 | 8 | 8 | 8 |
| Dimensionless gas velocity in the activator | 0.15 | 0.15 | 0.15 | 0.15 | 0.15 |
| Standard deviation value of the pressure pulsation at any point of the bed layer of the dense phase reaction zone maintained by supplementing fine particles, Pa | 500 | 500 | 500 | 500 | 500 |
| solid particle inventory of hydrogenation reactor:solid particle inventory of regeneration reactor:solid particle inventory of activation reactor | 40:3:3 | 40:3:3 | 40:3:3 | 40:3:3 | 40:3:3 |
| Height of the hydrogenation reactor:height of the regeneration reactor:height of the activation reactor | 5:1:1 | 5:1:1 | 5:1:1 | 5:1:1 | 5:1:1 |
| Diameter of the hydrogenation reactor:diameter of the regeneration reactor:diameter of the activation reactor | 4:1:1 | 4:1:1 | 4:1:1 | 4:1:1 | 4:1:1 |
| Expansion coefficient of the dense phase reaction zone | 1.64 | 1.58 | 1.61 | 1.56 | 1.55 |
| Maximum temperature difference in the reaction zone, ° C. | 7.1 | 8.2 | 7.3 | 7.5 | 7.5 |
| Carbon deposition content when the reaction time was 90 minutes under the high space velocity, % | could be controlled at no greater than 0.7% | could be controlled at no greater than 0.51% | could be controlled at no greater than 0.55% | could be controlled at no greater than 0.58% | could be controlled at no greater than 0.76% |

TABLE 2

| | Example 6 | Example 7 | Example 8 | Example 9 | Example 10 |
|---|---|---|---|---|---|
| Average mass flowrate (A1-A6 and B1-B5), kg/h | All 13 | All 13 | All 13 | All 13 | All 13 |
| Particle volume fractions for the pipelines (C1-C6 and D1-D5) | C1-C5 were 0.9%, C6 was 0.6%, D1-D5 were 1.2% | C1-C5 were 0.9%, C6 was 0.6%, D1-D5 were 1.2% | C1-C5 were 0.9%, C6 was 0.6%, D1-D5 were 1.2% | C1-C5 were 0.9%, C6 was 0.6%, D1-D5 were 1.2% | C1-C5 were 0.9%, C6 was 0.6%, D1-D5 were 1.2% |
| Ratio of the average mass flowrate of the supplement hydrogenation catalyst being transported to the hydrogenation catalyst inventory in the hydrogenation reactor, $h^{-1}$ | 0.00005 | 0.00005 | 0.00005 | 0.00005 | 0.00005 |
| Dimensionless particle diameter in the fluidized bed reactor | 10 | 10 | 10 | 10 | 10 |
| dimensionless gas velocity in the fluidized bed reactor | 0.05 | 7 | 0.1 | 0.1 | 0.1 |
| Dimensionless particle diameter in the regenerator | 8 | 8 | 1 | 36 | 8 |
| Dimensionless gas velocity in the regenerator | 0.15 | 0.15 | 0.05 | 5 | 0.15 |
| Dimensionless particle diameter in the activator | 8 | 8 | 8 | 8 | 1 |
| Dimensionless gas velocity in the activator | 0.15 | 0.15 | 0.15 | 0.15 | 0.05 |
| Standard deviation value of the pressure pulsation at any point of the bed layer of the dense phase reaction zone maintained by supplementing fine particles, Pa | 500 | 500 | 500 | 500 | 500 |
| solid particle inventory of hydrogenation reactor:solid particle inventory of regeneration reactor:solid particle inventory of activation reactor | 40:3:3 | 40:3:3 | 40:3:3 | 40:3:3 | 40:3:3 |
| Height of the hydrogenation reactor:height of the regeneration reactor:height of the activation reactor | 5:1:1 | 5:1:1 | 5:1:1 | 5:1:1 | 5:1:1 |
| Diameter of the hydrogenation reactor:diameter of the regeneration reactor:diameter of the activation reactor | 4:1:1 | 4:1:1 | 4:1:1 | 4:1:1 | 4:1:1 |
| Expansion coefficient of the dense phase reaction zone | 1.61 | 1.60 | 1.59 | 1.54 | 1.59 |
| Maximum temperature difference in the reaction zone, ° C. | 7.3 | 7.3 | 7.6 | 8.0 | 7.6 |
| Carbon deposition content when the reaction time was 90 minutes under the high space velocity, % | could be controlled at no greater than 0.72% | could be controlled at no greater than 0.72% | could be controlled at no greater than 0.74% | could be controlled at no greater than 0.8% | could be controlled at no greater than 0.76% |

TABLE 3

| | Example 11 | Example 12 | Example 13 | Example 14 | Example 15 |
|---|---|---|---|---|---|
| Average mass flowrate (A1-A6 and B1-B5), kg/h | All 13 | All 13 | All 13 | All 7 | All 26 |
| Particle volume fractions for the pipelines (C1-C6 and D1-D5) | C1-C5 were 0.9%, C6 was 0.6%, D1-D5 were 1.2% | C1-C5 were 0.9%, C6 was 0.6%, D1-D5 were 1.2% | C1-C5 were 0.9%, C6 was 0.6%, D1-D5 were 1.2% | C1-C5 were 0.83%, C6 was 0.55%, D1-D5 were 1.06% | C1-C5 were 1.1%, C6 was 0.7%, D1-D5 were 1.5% |
| Ratio of the average mass flowrate of the supplement hydrogenation catalyst being transported to the hydrogenation catalyst inventory in the hydrogenation reactor, $h^{-1}$ | 0.00005 | 0.00005 | 0.00005 | 0.00005 | 0.00005 |
| Dimensionless particle diameter in the fluidized bed reactor | 10 | 10 | 10 | 10 | 10 |
| dimensionless gas velocity in the fluidized bed reactor | 0.1 | 0.1 | 0.1 | 0.1 | 0.1 |
| Dimensionless particle diameter in the regenerator | 8 | 8 | 8 | 8 | 8 |
| Dimensionless gas velocity in the regenerator | 0.15 | 0.15 | 0.15 | 0.15 | 0.15 |
| Dimensionless particle diameter in the activator | 25 | 8 | 8 | 8 | 8 |
| Dimensionless gas velocity in the activator | 5 | 0.15 | 0.15 | 0.15 | 0.15 |
| Standard deviation value of the pressure pulsation at any point of the bed layer of the dense phase reaction zone maintained by supplementing fine particles, Pa | 500 | 700 | 1500 | 500 | 500 |
| solid particle inventory of hydrogenation reactor:solid particle inventory of regeneration reactor:solid particle inventory of activation reactor | 40:3:3 | 40:3:3 | 40:3:3 | 40:3:3 | 40:3:3 |
| Height of the hydrogenation reactor:height of the regeneration reactor:height of the activation reactor | 5:1:1 | 5:1:1 | 5:1:1 | 5:1:1 | 5:1:1 |
| Diameter of the hydrogenation reactor:diameter of the regeneration reactor:diameter of the activation reactor | 4:1:1 | 4:1:1 | 4:1:1 | 4:1:1 | 4:1:1 |
| Expansion coefficient of the dense phase reaction zone | 1.60 | 1.62 | 1.52 | 1.62 | 1.67 |
| Maximum temperature difference in the reaction zone, ° C. | 7.4 | 7.2 | 10.5 | 7.2 | 6.9 |
| Carbon deposition content when the reaction time was 90 minutes under the high space velocity, % | could be controlled at no greater than 0.75% | could be controlled at no greater than 0.7% | could be controlled at no greater than 0.7% | could be controlled at no greater than 0.93% | could be controlled at no greater than 0.47% |

TABLE 4

| | Example 16 | Example 17 | Example 18 | Comparative Example 1 | Comparative Example 2 |
|---|---|---|---|---|---|
| Average mass flowrate (A1-A6 and B1-B5), kg/h | All 13 | All 13 | All 13 | All 13 | System without regenerator and activator and without the supplement of the fresh catalyst and the fine particle catalyst |
| Particle volume fractions for the pipelines (C1-C6 and D1-D5) | C1-C5 were 0.9%, C6 was 0.6%, D1-D5 were 1.2% | C1-C5 were 0.9%, C6 was 0.6%, D1-D5 were 1.2% | C1-C5 were 0.9%, C6 was 0.6%, D1-D5 were 1.2% | C1-C5 were 0.7%, C6 was 0.3%, D1-D5 were 1.2% | |
| Ratio of the average mass flowrate of the supplement hydrogenation catalyst being transported to the hydrogenation catalyst inventory in the hydrogenation reactor, $h^{-1}$ | 0.00005 | 0.00005 | 0.00005 | 0.00005 | |
| Dimensionless particle diameter in the fluidized bed reactor | 10 | 10 | 10 | 10 | |
| dimensionless gas velocity in the fluidized bed reactor | 0.1 | 0.1 | 0.1 | 0.1 | |
| Dimensionless particle diameter in the regenerator | 8 | 8 | 8 | 8 | |
| Dimensionless gas velocity in the regenerator | 0.15 | 0.15 | 0.15 | 0.15 | |
| Dimensionless particle diameter in the activator | 8 | 8 | 8 | 8 | |
| Dimensionless gas velocity in the activator | 0.15 | 0.15 | 0.15 | 0.15 | |
| Standard deviation value of the pressure pulsation at any point of the bed layer of the dense phase reaction zone maintained by supplementing fine particles, Pa | 500 | 500 | 500 | No control, without the supplement of the fine particle catalyst | |
| solid particle inventory of hydrogenation reactor:solid particle inventory of regeneration reactor:solid particle inventoryof activation reactor | 30:1:1 | 40:3:3 | 40:3:3 | 40:3:3 | |
| Height of the hydrogenation reactor:height of the regeneration reactor:height of the activation reactor | 5:1:1 | 2:1:1 | 5:1:1 | 5:1:1 | |
| Diameter of the hydrogenation reactor:diameter of the regeneration reactor:diameter of the activation reactor | 4:1:1 | 4:1:1 | 6:1:1 | 4:1:1 | |
| Expansion coefficient of the dense phase reaction zone | 1.62 | 1.64 | 1.66 | 1.46 | 1.38 |
| Maximum temperature difference in the reaction zone, ° C. | 7.2 | 7.2 | 7.0 | 13.8 | 15.9 |

TABLE 4-continued

| | Example 16 | Example 17 | Example 18 | Comparative Example 1 | Comparative Example 2 |
|---|---|---|---|---|---|
| Carbon deposition content when the reaction time was 90 minutes under the high space velocity, % | could be controlled at no greater than 0.7% | could be controlled at no greater than 0.7% | could be controlled at no greater than 0.73% | could be controlled at no greater than 0.7% | 4.1% |

The invention claimed is:

1. A hydrogenation reaction process, comprising a hydrogenation step, a regeneration step, an activation step, and a recycling step, wherein:

in the hydrogenation step, nitrobenzene as a reaction raw material is contacted with hydrogen gas and a hydrogenation catalyst in a hydrogenation reactor to obtain aniline and a spent catalyst, wherein the hydrogenation reactor is a fluidized bed reactor, the hydrogenation catalyst is a copper-based catalyst comprising copper as a main active component supported on alumina or silica, and a full inventory of the cooper-based catalyst in the hydrogenation reactor is in contact with the reaction raw material;

in the regeneration step, the spent catalyst is regenerated in a fluidized bed regeneration reactor to obtain a regenerated catalyst;

in the activation step, the regenerated catalyst is activated in a fluidized bed activation reactor to obtain an activated catalyst; and in the recycling step, the activated catalyst is recycled to the hydrogenation step, wherein the process further comprises:

at least one hydrogenation degassing step of degassing the spent catalyst between the hydrogenation step and the regeneration step, at least one first regeneration degassing step of degassing the regenerated catalyst between the regeneration step and the activation step, at least one second regeneration degassing step of degassing the regenerated catalyst between the regeneration step and the recycling step, at least one activation degassing step of degassing the activated catalyst between the activation step and the recycling step, and a catalyst supplement step comprising introducing a supplement hydrogenation catalyst to the activation step, wherein the particle volume fraction in the unit of % in the transportation pipeline of the spent catalyst being transported from the hydrogenation step to the hydrogenation degassing step is C1, the particle volume fraction in the unit of % in the transportation pipeline of the spent catalyst being transported from the hydrogenation degassing step to the regeneration step is D1, the particle volume fraction in the unit of % in the transportation pipeline of the regenerated catalyst being transported from the regeneration step to the first regeneration degassing step is C2, the particle volume fraction in the unit of % in the transportation pipeline of the regenerated catalyst being transported from the first regeneration degassing step to the activation step is D2, the particle volume fraction in the unit of % in the transportation pipeline of the activated catalyst being transported from the activation step to the activation degassing step is C3, the particle volume fraction in the unit of % in the transportation pipeline of the activated catalyst being transported from the activation degassing step to the recycling step is D3, the particle volume fraction in the unit of % in the transportation pipeline of the regenerated catalyst being transported from the regeneration step to the second regeneration degassing step is C4, the particle volume fraction in the unit of % in the transportation pipeline of the regenerated catalyst being transported from the second regeneration degassing step to the recycling step is D4, the particle volume fraction in the unit of % in the transportation pipeline of the regenerated catalyst or the activated catalyst being transported from the recycling step to the hydrogenation step is C6, and wherein C1, C2, C3, C4, and C6 and D1, D2, D3, and D4 are in the range of 0.5-5%, wherein the hydrogenation reactor comprises a dense phase reaction zone, at least one dynamic pressure measuring point is mounted on the side wall of the dense phase reaction zone to measure an instantaneous pressure fluctuation in the dense phase reaction zone, and the catalyst supplement step is initiated when the standard deviation of the instantaneous pressure fluctuation is greater than 600 Pa, or when the catalyst particles having a particle diameter of less than 100 μm account for greater than 3 wt % by mass percent of all catalyst particles in the dense phase reaction zone.

2. The hydrogenation reaction process according to claim 1, wherein the supplement hydrogenation catalyst is a copper-based loaded catalyst having an average particle diameter of 5-150 μm.

3. The hydrogenation reaction process according to claim 1, wherein the hydrogenation catalyst has a bulk density of 300-1200 $kg/m^3$, and/or, the hydrogenation catalyst has an average particle diameter of 30-800 μm, and the catalyst particles having a particle diameter of less than 80 μm is not less than 2 wt % by mass percent of all catalyst particles.

4. The hydrogenation reaction process according to claim 1, wherein the catalyst supplement step is initiated when a response frequency of at least one dynamic pressure measuring point is not less than 100 Hz, and/or when the standard deviation of the instantaneous pressure fluctuation is greater than 1500 Pa, and/or when the catalyst particles having a particle diameter of less than 100 μm comprise greater than 5 wt % by mass percent of all catalyst particles in the dense phase reaction zone.

5. The hydrogenation reaction process according to claim 2, wherein the supplement hydrogenation catalyst has an average particle diameter of 20-70 μm.

6. The hydrogenation reaction process according to claim 3, wherein the hydrogenation catalyst has an average particle diameter of 50-600 μm, and/or the catalyst particles having a particle diameter of less than 80 μm comprise 5-15 wt % by mass percent of all catalyst particles.

7. The hydrogenation reaction process according to claim 1, wherein the average mass flowrate, in kg/h, of the spent catalyst being transported from the hydrogenation step to the hydrogenation degassing step is defined as A1, the average mass flowrate, in kg/h, of the spent catalyst being transported from the hydrogenation degassing step to the regeneration step is defined as B1, the average mass flowrate, in kg/h, of the regenerated catalyst being transported from the regeneration step to the first regeneration degassing step is defined as A2, the average mass flowrate, in kg/h, of the regenerated catalyst being transported from the first regeneration degassing step to the activation step is defined as B2, the average mass flowrate, in kg/h, of the activated catalyst being transported from the activation step to the activation degassing step is defined as A3, the average mass flowrate, in kg/h, of the activated catalyst being transported from the activation degassing step to the recycling step is defined as B3, the average mass flowrate, in kg/h, of the regenerated catalyst or the activated catalyst being transported from the recycling step to the hydrogenation step is defined as A6, then all of A1 to A3, A6 and B1 to B3 are 5-100 kg/h.

8. The hydrogenation reaction process according to claim 1, wherein the reaction conditions of the hydrogenation step comprise: the superficial gas velocity is 0.2-0.8 m/s, the molar ratio of hydrogen gas to nitrobenzene is 6-21, the reaction temperature is 220-280° C., the reaction pressure is 0.05-1 MPa, gauge pressure, and/or, the reaction conditions of the regeneration step comprise: in the presence of oxygen-containing gas, the superficial gas velocity is 0.1-0.6 m/s, the reaction temperature is 350-450° C., the reaction pressure is 0.05-1 MPa, gauge pressure, and/or, the reaction conditions of the activation step comprise: in the presence of hydrogen gas, the superficial gas velocity is 0.1-0.6 m/s, the reaction temperature is 200-250° C., the reaction pressure is 0.05-1 MPa, gauge pressure.

9. The hydrogenation reaction process according to claim 1, wherein the dimensionless particle diameter of the hydrogenation reactor is in the range of 1-60, and/or, the dimensionless particle diameter of the regeneration reactor is in the range of 1-40, and/or, the dimensionless particle diameter of the activation reactor is in the range of 1-30, wherein the dimensionless particle diameter is determined by the following equation:

$$\text{Dimensionless particle diameter} = \text{Average particle diameter} \times \sqrt[3]{\frac{\text{Gas density} \times \text{Gas} - \text{solid density difference} \times g}{\text{Gas kinetic viscosity}^2}},$$

wherein, the average particle diameter is the volume average particle diameter, in m, of solid particles in the reactor, the gas density is the density, in $kg/m^3$, of the gas in the reactor, the gas-solid density difference is the difference of the density, in $kg/m^3$, of solid particles minus the density, in $kg/m^3$, of the gas in the reactor, the gas kinetic viscosity is the kinetic viscosity, in Pa·s, of the gas in the reactor, and g is the absolute value of the gravity acceleration of 9.8 $m/s^2$.

10. The hydrogenation reaction process according to claim 1, wherein in the catalyst supplement step, the ratio of the average mass flowrate of the supplement hydrogenation catalyst being transported to the hydrogenation catalyst inventory in the hydrogenation reactor, in kg, is less than 10 $h^{-1}$.

11. The hydrogenation reaction process according to claim 1, wherein in the catalyst supplement step, the ratio of the average mass flowrate of the supplement hydrogenation catalyst being transported to the hydrogenation catalyst inventory in the hydrogenation reactor, in kg, is 0.00002-0.001 $h^{-1}$.

* * * * *